(12) United States Patent
Schock et al.

(10) Patent No.: US 7,892,271 B2
(45) Date of Patent: Feb. 22, 2011

(54) APPARATUS FOR ALTERING THE BODY TEMPERATURE OF A PATIENT

(75) Inventors: Robert B. Schock, Sparta, NJ (US); Marc Cote, Cornwall, NY (US)

(73) Assignee: Life Recovery Systems HD, LLC, Waldwick, NJ (US)

( * ) Notice: Subject to any disclaimer, the term of this patent is extended or adjusted under 35 U.S.C. 154(b) by 727 days.

(21) Appl. No.: 11/466,966

(22) Filed: Aug. 24, 2006

(65) Prior Publication Data

US 2006/0282142 A1    Dec. 14, 2006

Related U.S. Application Data

(63) Continuation-in-part of application No. 10/948,918, filed on Sep. 24, 2004, now Pat. No. 7,377,935.

(51) Int. Cl.
*A61F 7/00* (2006.01)

(52) U.S. Cl. .................... 607/108; 607/104

(58) Field of Classification Search ......... 607/104–112; 4/555, 559, 580, 585, 583; 601/15; 5/606, 5/928
See application file for complete search history.

(56) References Cited

U.S. PATENT DOCUMENTS

| | | | |
|---|---|---|---|
| 26,663 A | 1/1860 | French | |
| 998,804 A | 7/1911 | Salisbury | |
| 1,936,960 A | 11/1933 | Bowman | |
| 2,093,834 A | 9/1937 | Gaugler | |
| 2,272,481 A | 2/1942 | Rinkes et al. | |
| 2,471,302 A | 5/1949 | Nellie | |
| 2,493,067 A | 1/1950 | Goldsmith | |

(Continued)

FOREIGN PATENT DOCUMENTS

GB    1095988    12/1967

(Continued)

OTHER PUBLICATIONS

Bernard, S.A., et al., "Treatment of Comatose Survivors of Out-of-Hospital Cardiac Arrest with Induced Hypothermia", New England Journal of Medicine, Feb. 21, 2002, pp. 557-563, vol. 346, No. 8, Massachusetts Medical Society, Boston, Massachusetts, United States.

(Continued)

*Primary Examiner*—Roy D Gibson
(74) *Attorney, Agent, or Firm*—Armstrong Teasdale, LLP

(57) ABSTRACT

Apparatus for altering the body temperature of a patient comprises an enclosure defining an interior space for receiving at least a portion of a patient's body therein. The enclosure is constructed for transferring a heat transfer liquid into direct contact with the portion of the patient's body received in the enclosure to promote heat transfer between the patient's body and the heat transfer liquid. A drain for draining the heat transfer liquid from the interior space of the enclosure is at least partially disposed beneath the enclosure. A hold-open inhibits occlusion of the drain. A weir in fluid communication with the drain maintains the heat transfer liquid at a predetermined height in the enclosure. A control system is preprogrammed with a target temperature for the body temperature of the patient.

15 Claims, 25 Drawing Sheets

U.S. PATENT DOCUMENTS

| | | | |
|---|---|---|---|
| 2,566,600 A | 9/1951 | Colon | |
| 2,702,552 A | 2/1955 | Moodie | |
| 2,832,336 A | 6/1955 | Davis et al. | |
| 3,051,180 A | 8/1962 | Adams-Ray et al. | |
| 3,266,064 A | 8/1966 | Figman | |
| 3,477,424 A | 11/1969 | Tracy | |
| 3,587,577 A | 6/1971 | Smirnov et al. | |
| 3,670,347 A | 6/1972 | Weinstein | |
| 3,757,362 A | 9/1973 | Bowlin et al. | |
| 3,833,122 A * | 9/1974 | Cook | 210/207 |
| 3,866,994 A | 2/1975 | Bonin | |
| 4,057,861 A | 11/1977 | Howorth | |
| 4,068,326 A * | 1/1978 | Deschler | 4/541.3 |
| 4,074,369 A | 2/1978 | Harmon | |
| 4,139,004 A | 2/1979 | Gonzalez | |
| 4,141,585 A | 2/1979 | Blackman | |
| 4,149,529 A | 4/1979 | Copeland et al. | |
| 4,191,028 A | 3/1980 | Audet et al. | |
| 4,353,359 A | 10/1982 | Milbauer | |
| 4,376,437 A | 3/1983 | Sundheim et al. | |
| 4,442,838 A | 4/1984 | Samson et al. | |
| 4,572,188 A | 2/1986 | Augustine et al. | |
| 4,648,392 A | 3/1987 | Cartier et al. | |
| 4,691,762 A | 9/1987 | Elkins et al. | |
| 4,738,119 A | 4/1988 | Zafred | |
| 4,747,408 A | 5/1988 | Chuan-Chih | |
| 4,765,338 A | 8/1988 | Turner et al. | |
| D300,194 S | 3/1989 | Walker | |
| 4,858,259 A | 8/1989 | Simmons et al. | |
| 4,935,971 A * | 6/1990 | Dunn et al. | 4/559 |
| 4,945,901 A | 8/1990 | Burcke, Jr. | |
| 4,959,877 A | 10/1990 | Covil | |
| 4,962,761 A | 10/1990 | Golden | |
| 4,987,618 A | 1/1991 | Tolbert | |
| 4,987,896 A | 1/1991 | Nakamatsu | |
| 5,016,304 A | 5/1991 | Ryhiner | |
| 5,025,515 A * | 6/1991 | Rhines | 4/585 |
| 5,033,136 A | 7/1991 | Elkins | |
| 5,074,285 A | 12/1991 | Wright | |
| 5,146,625 A | 9/1992 | Steele et al. | |
| 5,149,331 A | 9/1992 | Ferdman et al. | |
| 5,172,689 A | 12/1992 | Wright | |
| 5,235,709 A | 8/1993 | Terlep | |
| 5,241,958 A | 9/1993 | Noeldner | |
| 5,243,706 A | 9/1993 | Frim et al. | |
| 5,246,061 A | 9/1993 | Zalite | |
| 5,249,318 A | 10/1993 | Loadsman | |
| 5,265,599 A | 11/1993 | Stephenson et al. | |
| 5,292,347 A | 3/1994 | Pompei | |
| 5,300,100 A | 4/1994 | Hickle et al. | |
| 5,305,471 A | 4/1994 | Steele et al. | |
| 5,305,542 A | 4/1994 | Phelps | |
| D347,491 S | 5/1994 | Holloway | |
| 5,330,519 A | 7/1994 | Mason et al. | |
| 5,336,250 A | 8/1994 | Augustine | |
| 5,342,411 A | 8/1994 | Maxted et al. | |
| 5,350,417 A | 9/1994 | Augustine | |
| 5,351,345 A * | 10/1994 | Sills et al. | 4/555 |
| 5,358,467 A | 10/1994 | Milstein et al. | |
| 5,383,918 A | 1/1995 | Panetta | |
| 5,405,370 A | 4/1995 | Irani | |
| 5,411,494 A | 5/1995 | Rodriguez | |
| 5,416,935 A | 5/1995 | Nieh | |
| D360,692 S | 7/1995 | Gambino | |
| 5,441,477 A | 8/1995 | Hargest | |
| 5,447,504 A | 9/1995 | Baker | |
| D365,378 S | 12/1995 | Wolfe | |
| D366,084 S | 1/1996 | Wolfe | |
| 5,507,792 A | 4/1996 | Mason et al. | |
| 5,584,084 A | 12/1996 | Klearman et al. | |
| 5,603,728 A | 2/1997 | Pachys | |
| 5,642,539 A | 7/1997 | Kuo | |
| D383,834 S | 9/1997 | Frankel | |
| 5,683,438 A | 11/1997 | Grahn | |
| 5,688,225 A | 11/1997 | Walker | |
| 5,722,482 A | 3/1998 | Buckley | |
| 5,755,756 A | 5/1998 | Freedman, Jr. et al. | |
| 5,800,383 A * | 9/1998 | Chandler et al. | 604/35 |
| 5,800,480 A | 9/1998 | Augustine et al. | |
| 5,814,009 A | 9/1998 | Wheatman | |
| 5,817,147 A | 10/1998 | Wolf | |
| D405,291 S | 2/1999 | Yu | |
| 5,871,526 A | 2/1999 | Gibbs et al. | |
| 5,887,304 A | 3/1999 | von der Heyde | |
| D410,084 S | 5/1999 | Tumey | |
| 5,913,885 A | 6/1999 | Klatz et al. | |
| 5,913,886 A | 6/1999 | Soloman | |
| 5,927,273 A | 7/1999 | Federowicz et al. | |
| 5,948,012 A | 9/1999 | Mahaffey et al. | |
| 5,950,234 A | 9/1999 | Leong et al. | |
| 5,957,964 A | 9/1999 | Ceravolo | |
| 5,975,081 A | 11/1999 | Hood et al. | |
| 5,989,285 A | 11/1999 | DeVilbiss et al. | |
| 5,991,948 A | 11/1999 | Stanley et al. | |
| 6,030,412 A | 2/2000 | Klatz et al. | |
| 6,052,853 A | 4/2000 | Schmid | |
| 6,079,070 A | 6/2000 | Flick | |
| 6,109,338 A | 8/2000 | Butzer | |
| 6,109,895 A | 8/2000 | Ray et al. | |
| 6,128,795 A | 10/2000 | Stanley et al. | |
| D433,508 S | 11/2000 | Crowther | |
| 6,149,674 A | 11/2000 | Borders | |
| 6,165,208 A | 12/2000 | Reyes et al. | |
| D436,175 S | 1/2001 | Tumey | |
| 6,182,316 B1 | 2/2001 | Thomas et al. | |
| 6,183,855 B1 | 2/2001 | Buckley | |
| D438,623 S | 3/2001 | Tantau | |
| 6,197,045 B1 | 3/2001 | Carson | |
| 6,210,427 B1 | 4/2001 | Augustine et al. | |
| 6,228,106 B1 | 5/2001 | Simbruner et al. | |
| 6,245,094 B1 | 6/2001 | Pompei | |
| 6,276,155 B2 | 8/2001 | Siman-Tov et al. | |
| 6,277,144 B1 | 8/2001 | Tomic-Edgar et al. | |
| 6,336,231 B1 * | 1/2002 | Smith | 4/580 |
| 6,656,208 B2 | 1/2002 | Grahn et al. | |
| 6,375,674 B1 | 4/2002 | Carson | |
| D461,900 S | 8/2002 | Siepmann | |
| 6,461,379 B1 | 10/2002 | Carson et al. | |
| 6,743,250 B2 | 12/2002 | Renfro | |
| 6,508,831 B1 | 1/2003 | Kushnir | |
| 6,517,510 B1 | 2/2003 | Stewart et al. | |
| 6,520,982 B1 | 2/2003 | Boynton et al. | |
| D474,061 S | 5/2003 | Cook | |
| 6,565,593 B2 | 5/2003 | Diana | |
| 6,585,709 B2 | 7/2003 | Maimets | |
| 6,602,277 B2 | 8/2003 | Grahn et al. | |
| 6,620,187 B2 | 9/2003 | Carson et al. | |
| 6,645,232 B2 | 11/2003 | Carson | |
| 6,660,027 B2 | 12/2003 | Gruszecki et al. | |
| 6,673,098 B1 | 1/2004 | Machold | |
| 6,673,099 B2 | 1/2004 | Grahn et al. | |
| 6,682,550 B2 | 1/2004 | Clifton et al. | |
| 6,685,731 B2 | 2/2004 | Kushnir et al. | |
| 6,692,518 B2 | 2/2004 | Carson | |
| 6,695,872 B2 | 2/2004 | Elkins | |
| 6,699,267 B2 | 3/2004 | Voorhees et al. | |
| 6,709,447 B1 | 3/2004 | Gammons | |
| 6,718,785 B2 | 4/2004 | Bieberich | |
| 6,730,115 B1 | 5/2004 | Heaton | |
| 6,739,001 B2 | 5/2004 | Flick et al. | |
| 6,749,624 B2 | 6/2004 | Knowlton | |
| 6,764,502 B2 | 7/2004 | Bieberich | |
| 6,799,063 B2 | 9/2004 | Carson | |
| 6,800,087 B2 | 10/2004 | Papay et al. | |

| | | | |
|---|---|---|---|
| 6,800,088 B1 | 10/2004 | Karapetyan | |
| 6,802,855 B2 | 10/2004 | Ellingboe et al. | |
| 6,818,012 B2 | 11/2004 | Ellingboe | |
| 6,855,158 B2 | 2/2005 | Stolpmann | |
| 6,969,399 B2 | 11/2005 | Schock et al. | |
| D527,822 S | 9/2006 | Trevino | |
| 7,380,302 B2 | 6/2008 | Gilchrest, Jr. et al. | |
| 2002/0116041 A1 | 8/2002 | Daoud | |
| 2002/0177837 A1 | 11/2002 | Barnitz | |
| 2003/0024684 A1 | 2/2003 | Lyons et al. | |
| 2003/0097163 A1 | 5/2003 | Kane et al. | |
| 2003/0125649 A1* | 7/2003 | McIntosh et al. | 601/15 |
| 2003/0195596 A1 | 10/2003 | Augustine et al. | |
| 2003/0236561 A1 | 12/2003 | Lennox | |
| 2004/0049252 A1 | 3/2004 | Gluderer | |
| 2004/0064170 A1 | 4/2004 | Radons et al. | |
| 2004/0064171 A1 | 4/2004 | Briscoe et al. | |
| 2004/0093050 A1 | 5/2004 | Beard et al. | |
| 2004/0158303 A1 | 8/2004 | Lennox et al. | |
| 2004/0186537 A1 | 9/2004 | Heaton et al. | |
| 2004/0187512 A9 | 9/2004 | Becker et al. | |
| 2004/0204748 A1 | 10/2004 | Hansen et al. | |
| 2004/0225341 A1 | 11/2004 | Schock et al. | |
| 2004/0243202 A1 | 12/2004 | Lennox | |
| 2004/0260369 A1 | 12/2004 | Schock et al. | |
| 2005/0027218 A1 | 2/2005 | Filtvedt et al. | |
| 2005/0060012 A1 | 3/2005 | Voorhees et al. | |
| 2005/0085882 A1 | 4/2005 | Grahn et al. | |
| 2005/0096714 A1 | 5/2005 | Freedman, Jr. et al. | |
| 2005/0103353 A1 | 5/2005 | Grahn et al. | |
| 2005/0107854 A1 | 5/2005 | Gammons et al. | |
| 2005/0283913 A1 | 12/2005 | Heaton et al. | |
| 2006/0069418 A1 | 3/2006 | Schock et al. | |
| 2008/0082150 A1 | 4/2008 | Schock et al. | |

FOREIGN PATENT DOCUMENTS

| | | |
|---|---|---|
| GB | 2263872 | 8/1993 |
| JP | 10/033626 | 2/1998 |
| WO | WO 88/10074 A1 | 12/1988 |
| WO | WO 94/05238 A1 | 3/1994 |
| WO | WO 96/13234 A1 | 5/1996 |
| WO | WO 98/40039 A1 | 9/1998 |
| WO | WO 99/09916 A1 | 3/1999 |
| WO | WO 99/39678 A1 | 8/1999 |
| WO | WO 99/44552 A1 | 9/1999 |
| WO | WO 01/50988 A1 | 7/2001 |
| WO | 2004023982 | 3/2004 |

OTHER PUBLICATIONS

Blair, D., et al., "The Increase in Tone in Forearm Resistance Blood Vessels Exposed to Increased Transmural Pressure", The Journal of Physiology, Jul. 1959, pp. 614-625, vol. 149, Cambridge University Press, London, Great Britain.

Felberg, R., et al., "Hypothermia After Cardiac Arrest: Feasibility and Safety of an External Cooling Protocol", Circulation, 2001, pp. 1799-1804, vol. 104, American Heart Association, Dallas, Texas, United States.

Future Medical Products, Inc., "Enhanced External Counterpulsation (EECP) Fact Sheet", Mar. 1994, pp. 1-3.

Grahn, D., et al., "Recovery from Mild Hypothermia can be Accelerated by Mechanically Distending Blood Vessels in the Hand", Journal of Applied Physiology, Nov. 1998, pp. 1643-1648, vol. 85, No. 5, The American Physiological Society, Bethesda, Maryland, United States.

Henriksen, O., "Local Sympathetic Reflex Mechanism in Regulation of Blood Flow in Human Subcutaneous Adipose tissue", ACTA Physiologica Scandinavica, 1977, 48 pages, Supplement 450, Almqvist & Wiksell, Uppsala, Sweden.

Henriksen, O., "Sympathetic Reflex Control of Blood Flow in Human Peripheral Tissues", ACTA Physiologica Scandinavica, 1991, pp. 33-39, vol. 143, Supplement 603, ACTA Physiologica Scandinavica, Stockholm, Sweden.

Holzer, M., et al., "Mild Therapeutic Hypothermia to Improve the Neurologic Outcome after Cardiac Arrest", New England Journal of Medicine, Feb. 21, 2002, pp. 549-556, vol. 346, No. 8, Massachusetts Medical Society, Boston, Massachusetts, United States.

Oakley, E., et al., "Can Recovery From Mild Hypothermia be Accelerated so Much by Mechanically Distending Locally Heated Blood Vessels?", Journal of Applied Physiology, Aug. 1999, pp. 867-868, vol. 87, No. 2, The American Physiology Society, Bethesda, Maryland, United States.

Janicki, et al., "Comparison of Two Different Temperature Maintenance Strategies During Open Abdominal Surgery", Anesthesiology, Oct. 2001, pp. 868-874, vol. 95.

Kirklin, et al., "Hypothermia, Circulatory Arrest, and Cardiopulmonary Bypass", Chapter 2, 1993, pp. 113-114, vol. 1, Second Edition, Churchill Livingston.

Koscheyev et al., "Augmentation of Blood Circulation to the Fingers by Warming Distant Body Areas", European Journal of Applied Physiology and Occupational Physiology (2000), pp. 103-111, 82.

Lawson, W.E., et al., "Efficacy of Enhanced External Counter-pulsation in the Treatment of Angina Pectoris", 1992, p. 1.

Mellergard, "Changes in Human Intracerebral Temperature in Response to Different Methods of Brain Cooling", Neurosurgery, Oct. 1992, pp. 671-677, vol. 31, No. 4.

Nag, et al., "Efficacy of a Water-Cooled Garment for Auxiliary Body Cooling in Heat", Ergonomics, 1998, pp. 179-187, vol. 41, No. 2.

Nesher, et al., "A Novel Thermoregulatory System Maintains Perioperative Normothermia in Children Undergoing Elective Surgery", Pediatric Anesthesia, 2001, pp. 555-560.

Oster, M.D., "Guidelines for the Submission of Abstracts", Apr. 30, 1993, p. 1.

Plattner, et al., "Efficacy of Intraoperative Cooling Methods", Anesthesiology, Nov. 1997, pp. 1089-1095, vol. 87(5), printed from www.anesthesiology.org.

Raven, et al., "Hemodynamic Changes During Whole Body Surface Cooling and Lower Body Negative Pressure", Aviation, Space, and Environmental Medicine, Jul. 1981, pp. 387-391.

Taguchi, A., et al., "Negative Pressure Rewarming vs. Forced Air Warming in Hypothermic Postanesthetic Volunteers", Anesthesia & Analgesia, Jan. 2001, pp. 261-266, vol. 92, No. 1, International Anesthesia Research Society et al., San Francisco, California, United States.

Wolthuis, R., et al., "Physiological Effects of Locally Applied Reduced Pressure in Man", Physiological Reviews, 1974, pp. 566-595, vol. 54, The American Physiological Society, Bethesda, Maryland, United States.

"Treatment of Refractory Fever in Neurosciences Critical Care Unit Using a Novel, Water-Circulating Cooling Device", Journal of Neurosurgical Anesthesiology, vol. 15, No. 4, pp. 313-318, 2003.

Effects of Inducted Hypothermia on Samatosensory Evoked Potentials in Patients with Chronic Spinal Cord Injury, Paraplegia 31, 730-741, 1993.

Gardella et al., "Lowering Body Temperature with a Cooling Suit as Symptomatic Treatment for Thermosensitive Multiple Scherosis Patients", Ital. J. Neurol. Sci., 1995.

Syndulko et al., "Preliminary Evaluation of Lowering Tympani Temperature for the Symptomatic Treatment of Multiple Sclerosis", J. Neuro. Rehab., vol. 9, No. 4, 1995.

Ku et al., "Hemodynamic and Thermal Responses to Head and Neck Cooling in Men and Women", Am J Phys Med Rehabil, 75:443-450, 1996.

Spinoff, "New Help for MS Patients" 1993.

"Acute Effects of Cooling in Multiple Sclerosis: Pilot Study to Compare Two Cooling Garments", 1995.

Flensner et al., "The Cooling-Suit: Case Studies of its Influence on Fatigue Amoung Eight Individuals with Multiple Sclerosis", Journal of Advanced Nursing 37(6), 541-550, Mar. 2002.

Ku et al., "Physiologic and Functional Responses of MS Patients to Body Cooling", Multiple Sclerosis, Sep./Oct. 2000, 427-434.

Regan et al., "Effect of body temperature on visual evoked potential delay and visual perception in multiple sclerosis", Journal of Neurology, Neurosurgery, and Psychiatry, 1977, 40, 1083-1091.

Greenleaf, et al., Fluid-electrolyte shifts and thermoregulation: Rest and work in heat with head cooling, Aug. 1980, vol. 51, No. 8, ASEMCG 5(8): 747-850.

International Search Report dated Jan. 31, 2006 regarding PCT/US05/33044, 3 pages.

International Search Report for PCT/US07/76534, dated Oct. 3, 2008, 3 pages.

* cited by examiner

APPARATUS FOR ALTERING THE BODY TEMPERATURE OF A PATIENT

CROSS-REFERENCE TO RELATED APPLICATION

This application is a continuation-in-part of co-pending U.S. application Ser. No. 10/948,918 filed Sep. 24, 2004, which is incorporated herein by reference in its entirety.

BACKGROUND OF THE INVENTION

This invention generally relates to medical apparatus for altering the body temperature of a patient and more particularly to apparatus that enables efficient, quick adjustment of the body temperature of a patient, especially to induce hypothermia.

Sudden cardiac arrest remains a serious public health issue. Approximately 350,000 individuals are stricken in the United States annually, with overall survival rates of roughly 5 percent. Even with the immediate availability of the most advanced care currently available, including cardiopulmonary resuscitation (CPR), drugs, ventilation equipment, and automatic external defibrillators, a survival rate of 25 percent may be the probable best case scenario. Improved therapies to deal with this condition are clearly needed.

Numerous incidences of recovery following accidental hypothermia and cardiac arrest have been reported. This observation has led researchers to consider therapeutic hypothermia as a possible treatment for reducing the adverse consequences of circulatory arrest. Various studies have shown that mild systemic hypothermia (approximately 3-5° C. (5.4-9.0° F.)) can reduce damage to vital organs, including the brain. Hypothermia induced both during and following cardiac arrest has demonstrated this benefit. The use of cardiopulmonary bypass has also been effective in rapidly achieving this goal. Direct flushing of cooled fluids into the arterial system has also been employed with success. Both invasive measures, however, require large bore intravascular catheters and rapid introduction of sterile solutions into the patient. Such invasive approaches have obvious disadvantages in dealing with out-of-hospital emergencies.

Noninvasive cooling, if sufficiently effective and portable, would be a preferable approach. Direct cooling of the head alone has produced variable results. However, post-resuscitative cooling of the entire body to approximately 33° C. (91.4° F.) by noninvasive treatment has been demonstrated to be surprisingly effective in recent clinical studies. The use of cold gel and ice packs produced cooling of approximately 0.9° C. (1.6° F.) per hour, and resulted in a nearly 100 percent improvement in neurologically intact survival (Bernard S. A. et al., *Treatment of Comatose Survivors of Out-of-Hospital Cardiac Arrest with Induced Hypothermia*, 346 New Eng. J. Med. 557-563 (2002)). In another study, cold air was found to be capable of cooling patients at a rate of about 0.25° C. (0.45° F.) per hour, which caused a 40 percent improvement in the same endpoint (Sterz F. et al., *Mild Therapeutic Hypothermia to Improve the Neurologic Outcome after Cardiac Arrest*, 346 New Eng. J. Med. 549-556 (2002)). In yet another study, a combination of water-filled cooling blankets and ice packs applied to the skin resulted in a cooling rate of 0.8° C. (1.4° F.) per hour (Felberg et al., *Hypothermia After Cardiac Arrest—Feasibility and Safety of an External Cooling Protocol*, 104 Circulation 1799-1804 (2001)). It is believed that increasing the rate of cooling from what is shown in these studies may produce a higher rate of patient salvage.

SUMMARY OF THE INVENTION

In one aspect of the present invention, apparatus for altering the body temperature of a patient generally comprises an enclosure defining an interior space for receiving at least a portion of a patient's body therein. The enclosure is constructed for transferring a heat transfer liquid into direct contact with the portion of the patient's body received in the enclosure to promote heat transfer between the patient's body and the heat transfer liquid. A drain drains the heat transfer liquid from the interior space of the enclosure. At least a portion of the drain is disposed beneath the enclosure, and a hold-open is disposed to hold the drain open to inhibit occlusion of the drain.

In another aspect of the present invention, apparatus for adjusting the core body temperature of a patient generally comprises an enclosure defining an interior space for receiving at least a portion of a patient's body therein. An inlet in the enclosure allows a heat transfer liquid to flow into the enclosure for direct contact with the portion of the patient's body received in the enclosure to promote heat transfer between the patient's body and the heat transfer liquid. A liquid delivery system directs the heat transfer liquid to flow through the inlet of the enclosure into the interior space of the enclosure. A control unit generally comprises a power source, a control system, and a user interface for powering and controlling the liquid delivery system. The control system is preprogrammed with a target temperature for the core body temperature of the patient.

In yet another aspect of the present invention, apparatus for adjusting the body temperature of a patient generally comprises an enclosure defining an interior space for receiving at least a portion of a patient's body therein. An inlet in the enclosure allows a heat transfer liquid to flow into the enclosure for direct contact with the portion of the patient's body received in the enclosure to promote heat transfer between the patient's body and the heat transfer liquid. An outlet in the enclosure allows the heat transfer liquid to be exhausted from the enclosure. A weir in fluid communication with the outlet maintains the heat transfer liquid at a predetermined height in the enclosure.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE INVENTION

Figure 1:
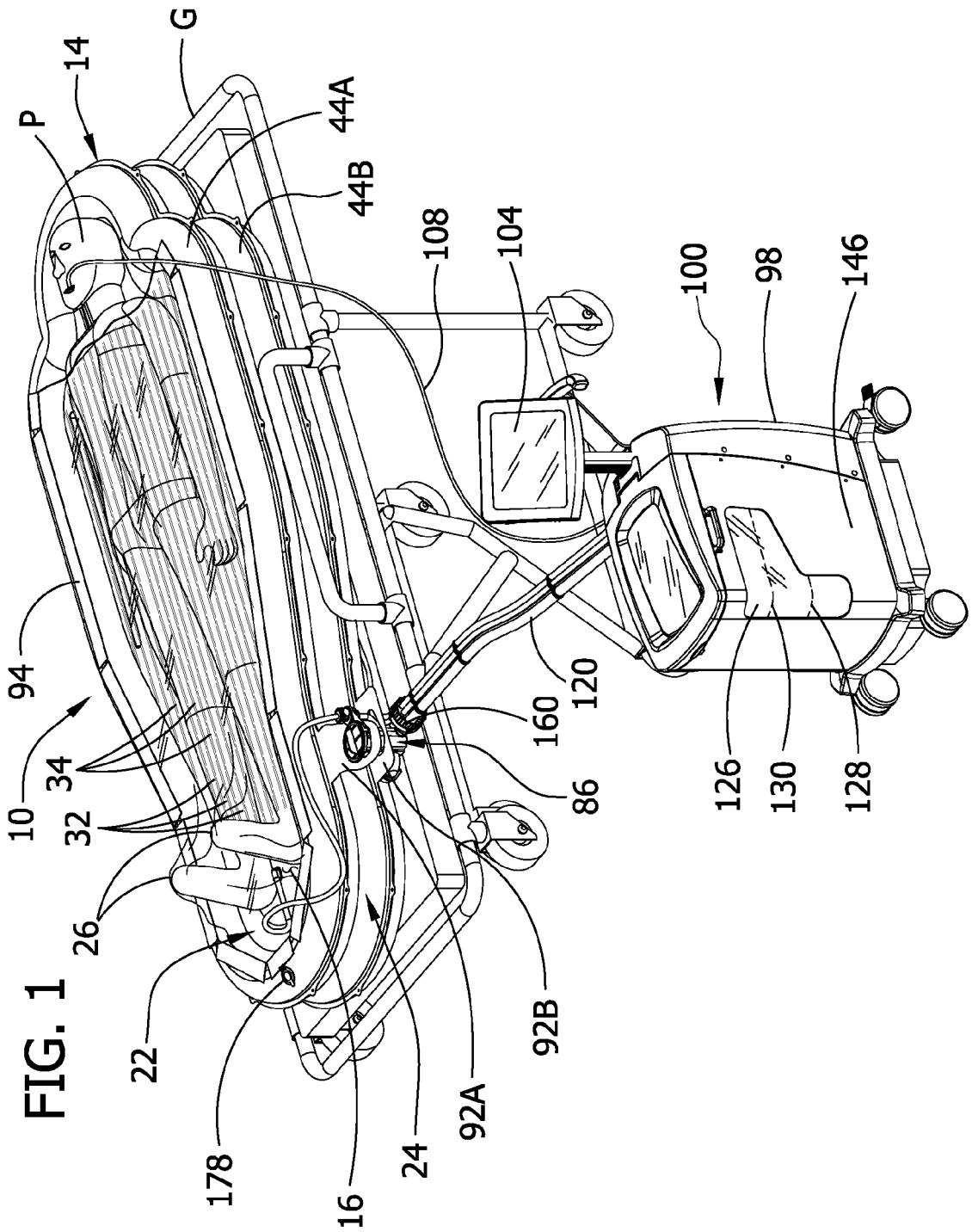
FIG. 1 is a perspective of an apparatus of the present invention in use for altering the body temperature of a patient lying in the apparatus on a gurney.
Figure 2:
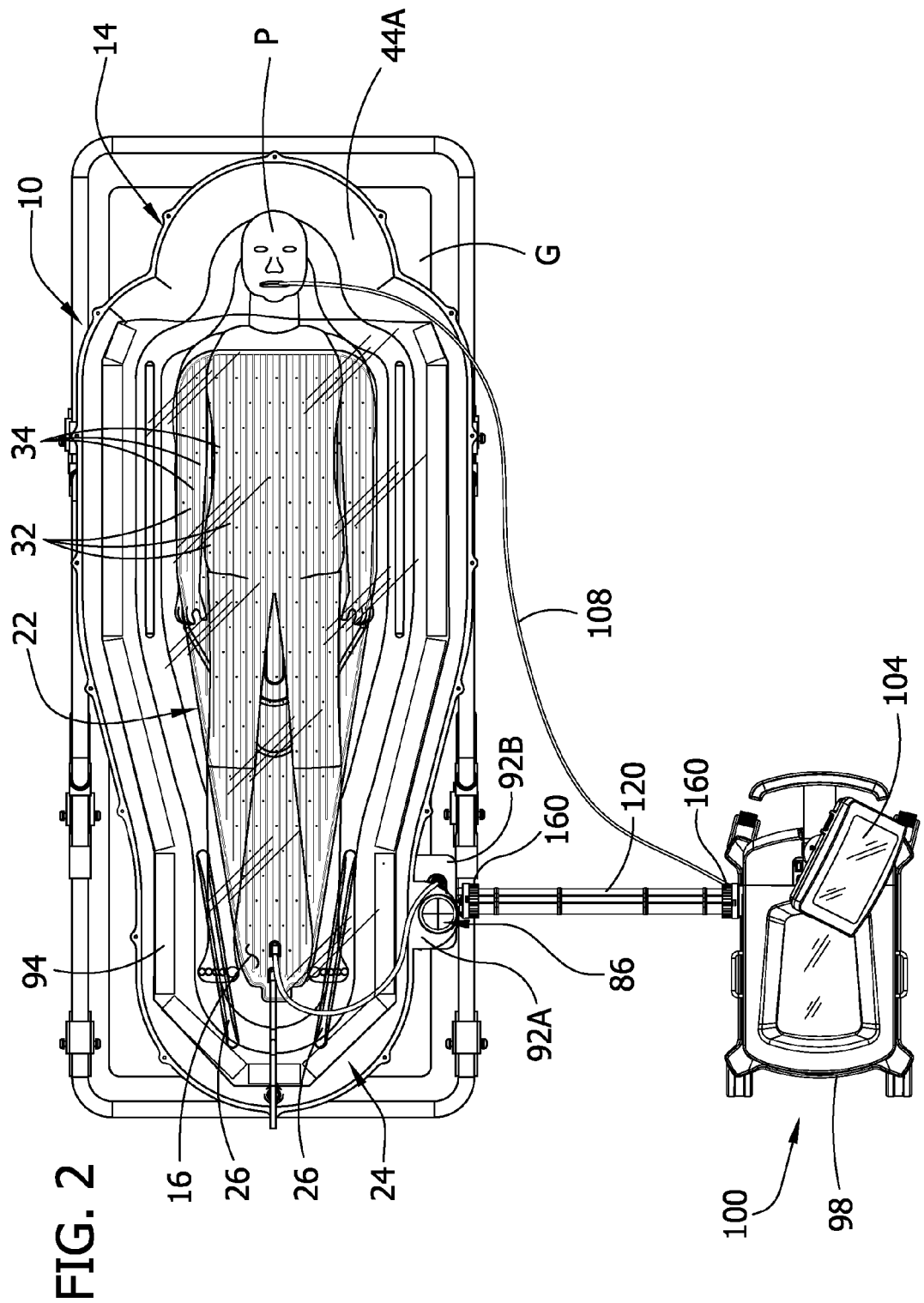
FIG. 2 is a top plan of the apparatus of FIG. 1.
Figure 3:
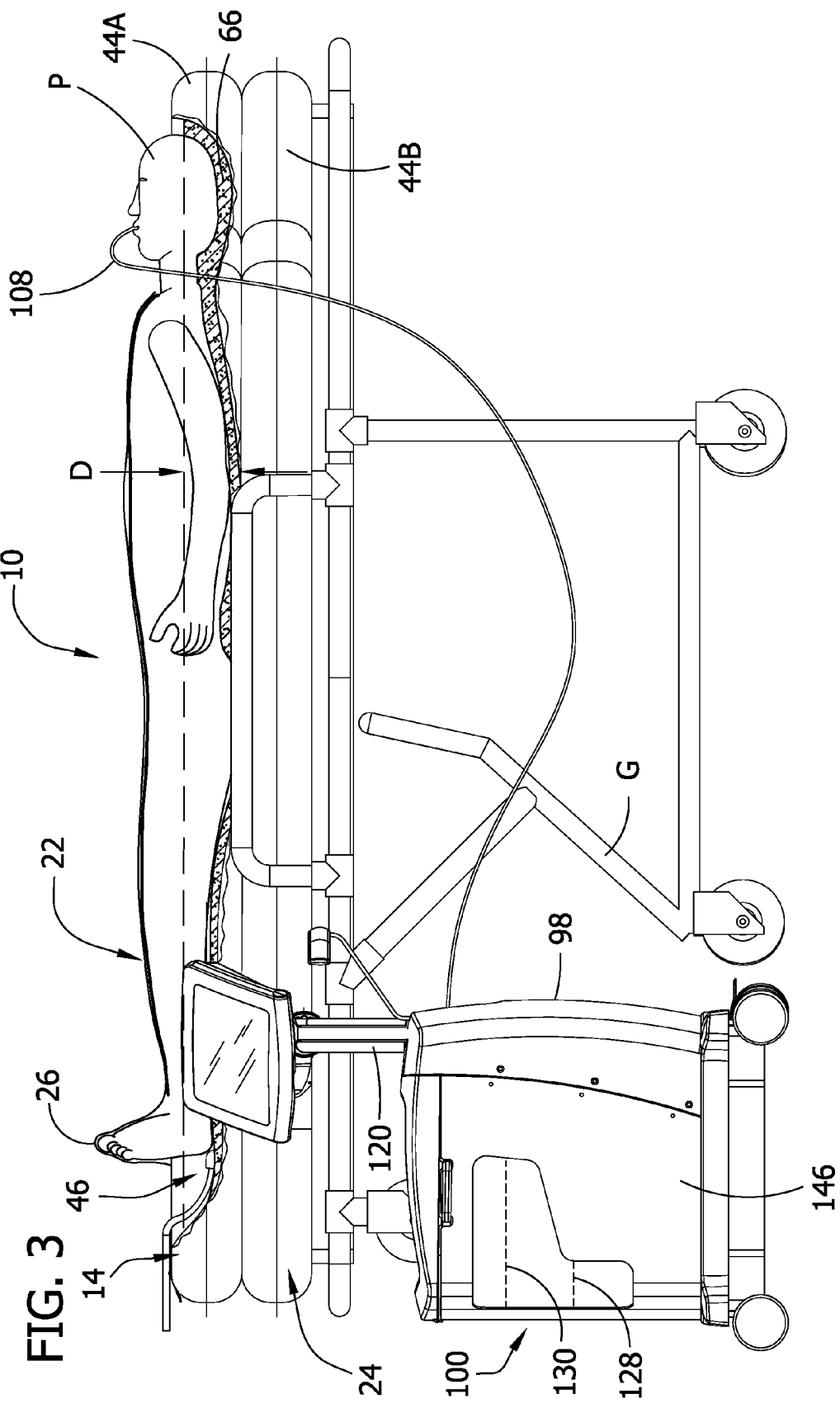
FIG. 3 is a side view of the apparatus with portions of an enclosure thereof broken away.

Referring now to the drawings and particularly to FIGS. 1-3, reference number 10 generally indicates an apparatus for adjusting the body temperature of a patient P. The apparatus 10 generally comprises an enclosure, indicated at 14, defining an interior space 16 for receiving a patient's body. The enclosure 14 is adapted to allow heat transfer liquid 18 (FIG. 17), such as water, saline, or other suitable liquids, to flow into the interior space 16 for direct contact with the patient's body to promote heat transfer between the patient P and the heat transfer liquid. In the illustrated embodiment, the interior space 16 of the enclosure 14 is configured to receive the entire body of the patient P, including the torso, arms, and legs (FIGS. 1-3). As a result, the amount of surface area of the patient P available for contact by the heat transfer liquid 18 is maximized. It is to be understood that the enclosure 14 can be configured to receive less than the patient's entire body. That is, the enclosure 14 can be configured to receive only a portion of the patient's body.

The enclosure 14 is adapted to generally conform to the shape of the body of the patient P received therein to accommodate patients of various shapes and sizes. For example, in the illustrated configuration, the enclosure 14 is suitable for patients having a size between about the 5th percentile and about the 95th percentile adult male. Other enclosures adapted to receive smaller patients (e.g., babies, children, small adults) or larger patients are also contemplated. Although the patient P is most commonly a human, the apparatus 10 could be configured for and used for altering the body temperature of other animals. More detail regarding the conforming shape of the enclosure 14 is provided below.

As illustrated in FIGS. 1-3, the enclosure 14 comprises a cover, indicated at 22, for overlying the patient P from the neck downward, and a compliant support, indicated at 24, for underlying the patient's entire body. As shown in FIGS. 2 and 3, the cover 22 is limp so that it generally conforms, under its own weight, to the contours of the upward facing surface of the patient's body it is covering. To this end, the cover 22 includes two foot gussets 26 located in a portion of the cover adapted to receive the feet of the patient P. The foot gussets 26 allow the cover 22 to more readily conform to the contours of the patient P near the feet of the patient. Each of the foot gussets 26 comprise a pocket for receiving a respective foot of the patient P thereby preventing the feet of the patient from creating a tent affect in the cover 22 (FIG. 3). In other words, each of the foot gussets 26 are sized and shaped for receiving and conforming to one of the feet of the patient P. It is to be understood that the foot gusset can be formed as a single pocket adapted to receive both of the patient's feet therein.

With reference to FIGS. 4-7, the cover 22 comprises a generally limp sheet-like body-facing component 28 and a generally limp sheet-like outer component 30 that are in face-to-face engagement with one another. In the illustrated configuration, the outer component 30 is significantly smaller than the body-facing component 28 to conserve material. It will be understood that the outer component 30 and body-facing component 28 can have the same size, or the outer component can have a size greater than the body-facing component.

The body-facing and outer components 28, 30 are liquid impermeable and joined to one another along their facing sides to form a plurality of passages 32 therebetween for allowing the heat transfer liquid 18 to flow through the cover 22. Heat sealing is used to seal the components 28, 30 together along seams 34 to form the passages 32 because it provides adequate strength without requiring additional raw materials (e.g., adhesive). Other methods of forming the passages 32 or sealing the components 28, 30 to one another, such as adhesives, are also contemplated as being within the scope of the present invention.

Figure 4:
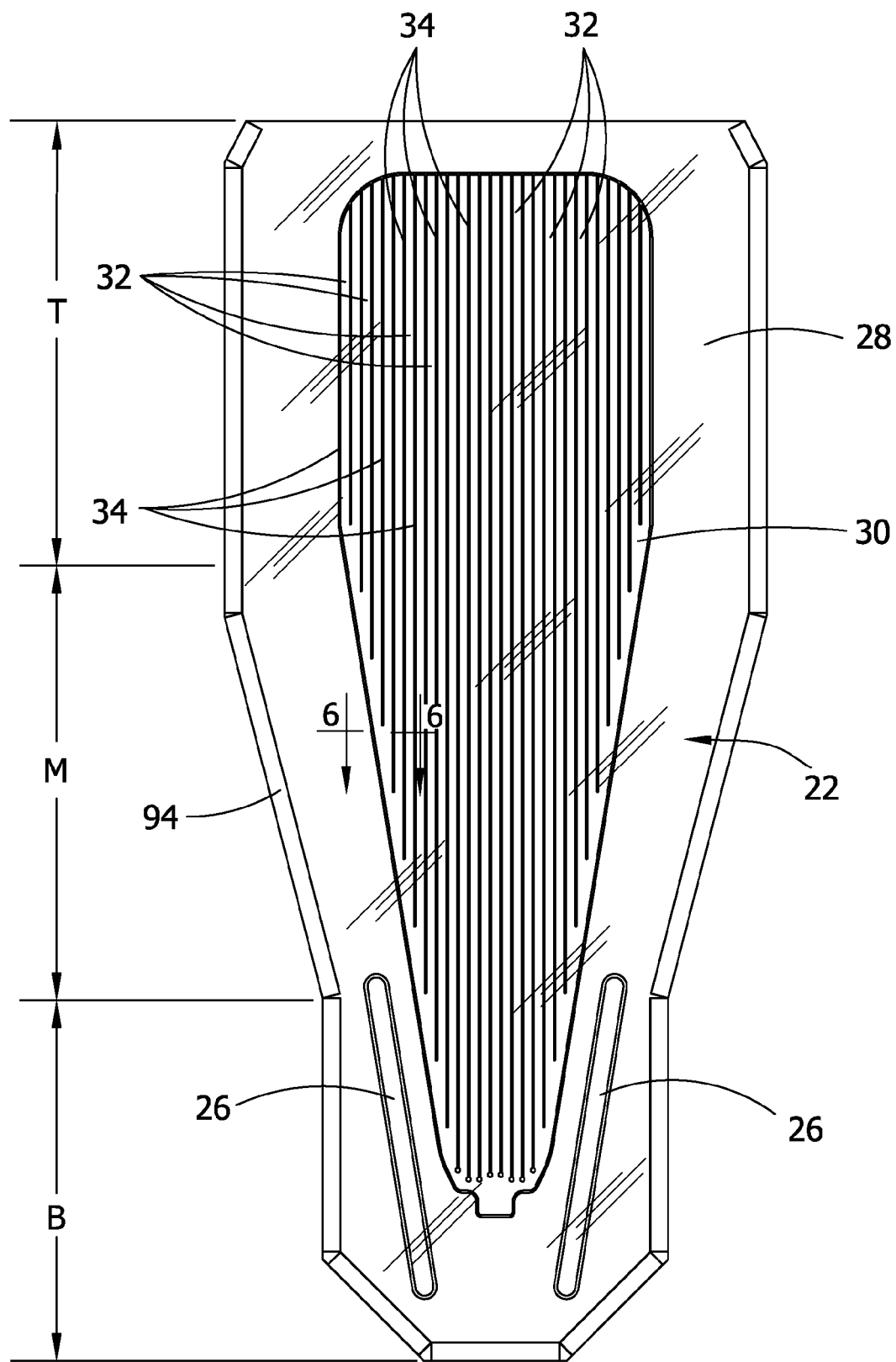
FIG. 4 is a top plan of a cover of the enclosure.

The passages 32 in the cover 22 are configured to distribute heat transfer liquid 18 over a large portion of the surface area of the patient's body. Specifically, the illustrated cover 22 is configured to distribute heat transfer liquid 18 over the patient P from the neck downward (see, FIGS. 1 and 2). As illustrated in FIG. 4, each of the passages 32 extend generally longitudinally of the enclosure 14 and have a width of approximately 25 mm and a height of approximately 3 mm. It is to be understood that the dimensions provided for the passages 32 are exemplary only and that the passages can be formed to have various dimensions. It is also understood that the passages 32 can extend in directions relative to the enclosure 14 other than longitudinal (e.g., lateral, oblique) and need not be parallel to one another.

Figure 6:
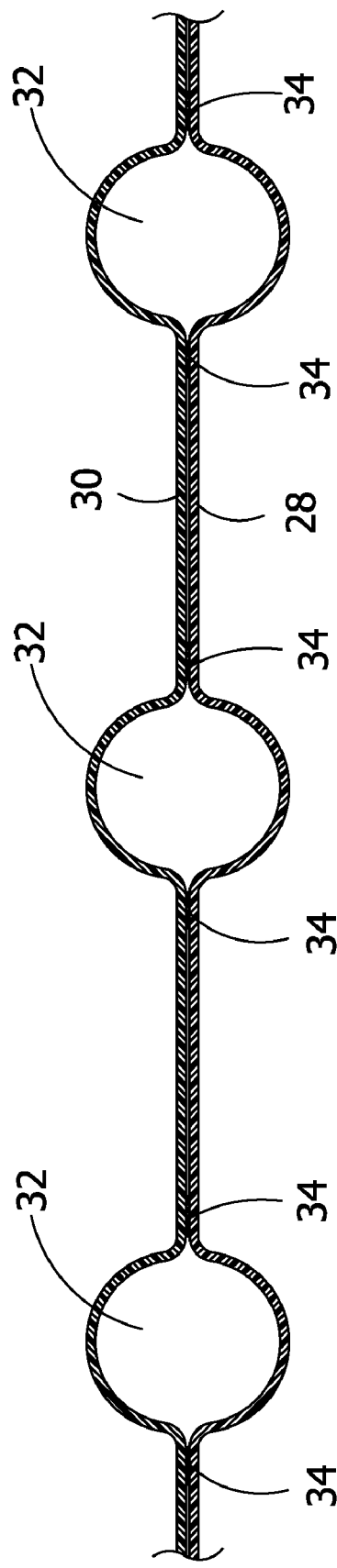
FIG. 6 is an enlarged fragmentary section on line 6-6 of FIG. 4.

Before the passages 32 are filled with heat transfer liquid 18, the sheet-like body-facing component 28 and sheet-like outer component 30 of the passage generally lie flat against one another. Once heat transfer liquid 18 flows inside the passage 32, however, the cross-sectional area of the passage increases to allow heat transfer liquid to flow between the components 28, 30 (FIG. 6). The weight of the heat transfer liquid 18 in the passages 32 causes the cover 22 to further conform to the contours of the patient's body. Since the passages 32 extend throughout much of the cover 22, the majority of the cover is weighted against the body of the patient P by the heat transfer liquid. It is to be understood that the passages 32 formed in the cover 22 can have hold-opens (not shown) for maintaining the increased cross-sectional area of the passages even when heat transfer liquid is not flowing through the passages. Hold-opens are described in further detail below.

Figure 5:
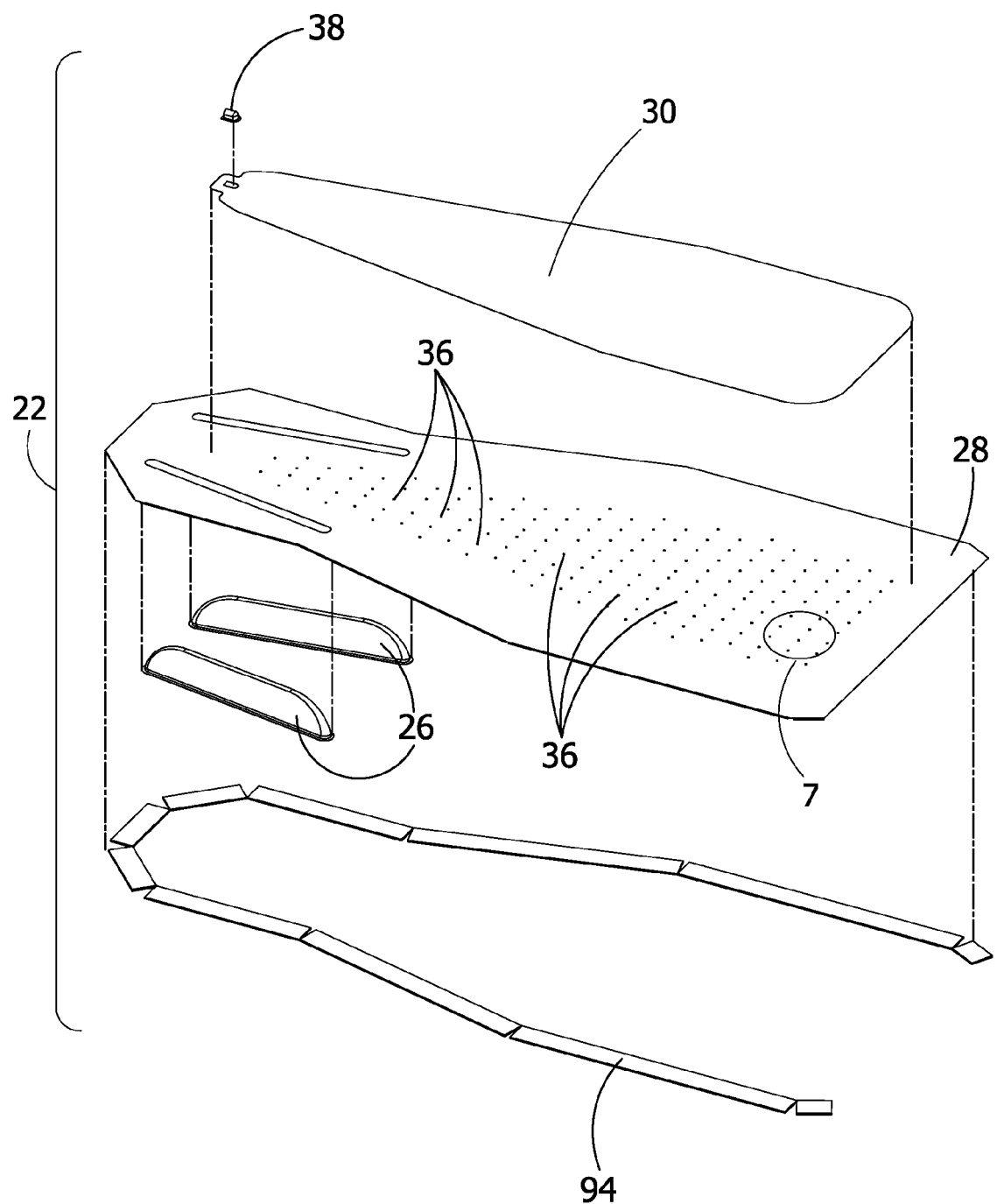
FIG. 5 is an exploded perspective of the cover.
Figure 7:
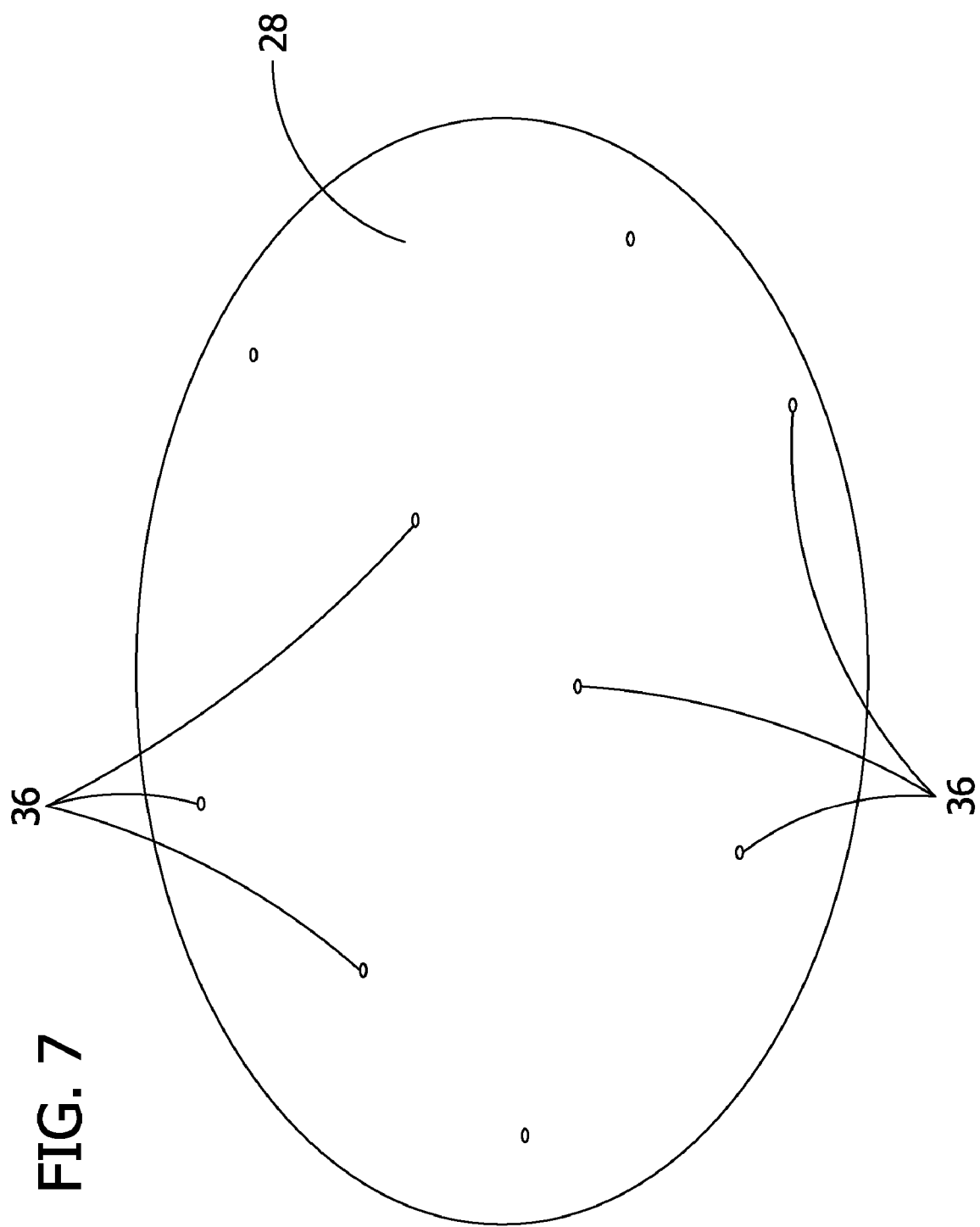
FIG. 7 is an enlargement of a fragment of the cover as indicated in FIG. 5.

The body-facing component 28 of the cover 22 includes a plurality of openings 36 (i.e., inlets) therein corresponding to the passages 32 for allowing the heat transfer liquid 18 to pass from the passages to the portion of the patient's body received in the enclosure 14 (FIGS. 5 and 7). Each opening 36 is generally circular and preferably has a diameter of about 1 millimeter (0.04 inches). The openings 36 are shown enlarged in the accompanying Figures so that they can be seen. The small diameter openings 36 restrict the flow of heat transfer liquid 18 from the passages 32 into the enclosure 14 thereby causing the entire length of the passages to fill with heat transfer liquid. As a result, the heat transfer liquid 18 is evenly distributed via the passages 32 to each of the openings 36. A doghouse connector 38 is affixed to the outer component 30 of the cover 22 for fluidly connecting the passages 32 in the cover to a liquid delivery system. The liquid delivery system is described in detail below.

The number of openings 36 positioned in various portions of the cover 22 may be varied to regulate the distribution of heat transfer liquid 18 throughout the enclosure 14. As illustrated in FIG. 5, the openings 36 in the cover 22 are positioned for generally evenly distributing the heat transfer liquid 18 over the top of the patient's body. Heat transfer liquid 18 is directed through the doghouse connector 38 and into the passages 32 such that the heat transfer liquid flows from a bottom section B (i.e., the lower one-third) of the cover 22, through a middle section M (i.e., the middle one-third) of the cover to a top section T (i.e., the top one-third) of the cover (FIG. 4). To even the flow distribution, the number of openings 36 increases along the length of the passages 32 in a direction away from the bottom section B of the cover 22 (FIG. 5). Thus, the middle section M of the cover 22 has a greater number of openings 36 than the bottom section B, and the top section T has a greater number of openings than the middle section.

In another configuration (not shown), the diameters of the openings 36 are varied along the length of the passages 32 in a direction away from the bottom section B of the cover 22. Using this approach, openings 36 having smaller diameters are positioned near the bottom sections B of the cover 22 while openings with progressively larger diameters are positioned in the middle and top sections M, T of the cover.

It is to be understood that numerous configurations for the openings 36 are possible to adequately distribute heat transfer liquid 18 to the body of the patient P by varying the size, shape, and distribution of the openings. It is also understood that the openings 36 in the cover 22 may be positioned to distribute heat transfer liquid 18 unevenly throughout the interior space 16 of the enclosure 14. By having an uneven flow distribution, a greater volume of heat transfer liquid 18 can be directed to selected portions of the patient's body, such as those more amenable to heat transfer (e.g., the head, neck, torso), than other non-selected portions of the patient's body, which are also received in the enclosure 14.

The configuration of the passages 32 and openings 36 illustrated in FIGS. 4 and 5 is particularly useful where CPR is to be administered to the patient P while the patient is in a supine position in the interior space 16 of the enclosure 14. During CPR the chest of the patient P is compressed through the limp cover 22 generally along the medial line of the patient. As a result, any passages 32 in the cover 22 corresponding approximately with the medial line of the patient P could be repeatedly blocked as the patient's chest is compressed thereby reducing the flow of heat transfer liquid 18 to the interior space 16 of the enclosure 14. Since a number of the passages 32 and openings 36 are offset from the medial line of the patient P, the chest compressions performed during CPR are less disruptive of fluid flow through the enclosure 14. In other words, chest compressions can be performed on the patient P while the patient is received in the interior space 16 of the enclosure 14 (i.e., directly through the cover 22) with minimal disruption of flow of heat transfer liquid 18 to the patient.

In the illustrated embodiment, the cover 22 is made of a transparent material, such as polyvinyl chloride (PVC), polyethylene, or polyurethane, so that the body of the patient P received within the interior space 16 of the enclosure 14 can be viewed through the cover. It is to be understood, however, that the cover 22 can be made of a non-transparent material or have a portion that is transparent and a portion that is non-transparent.

With reference now to FIGS. 8-12, the compliant support 24 is a pneumatic support, which (like the cover 22) generally conforms to the shape of the patient's body when the body rests on the support. Moreover, the compliant support 24 minimizes pressure concentrations beneath the patient P which facilitates the flow of heat transfer liquid 18 beneath the patient and minimizes the possibility of pressure sores developing in the skin of the patient. Generally, the compliant support 24 comprises an inflatable base 42 (broadly, a "first zone"), which is the portion of the compliant support upon which the patient P rests, and two generally oblong, inflatable tubes 44A, 44B (broadly, a "second zone") forming a periphery around the base. In the illustrated embodiment, one of the inflatable tubes 44A is arranged on top of the other tube 44B. It is to be understood, however, that more or fewer (i.e., one) inflatable tubes 44A, 44B can be used to form the periphery of the base 42. It is also to be understood that the inflatable tubes could be disposed side-by-side instead of one on top of the other.

The stacked inflatable tubes 44A, 44B and base 42 cooperatively form a watertight well, generally indicated at 46, for receiving the entire body of the patient P therein. The well 46 is configured to generally conform to the body of the patient P thereby minimizing the volume of the interior space 16 of the enclosure 16 and the amount of heat transfer liquid 18 necessary to effectively alter the body temperature of the patient P. More specifically, the patient P is positioned in a supine position on the base 42 with the base and the tubes 44A, 44B in a deflated state. The base 42 and inflatable tubes 44A, 44B are then inflated to enclose the patient's body within the well 46 and generally conform the well to the profile of the patient's body. As the inflatable tubes 44A, 44B are filled with air (or other suitable gas), the tubes generally conform to the sides of the patient P. The base 42 is typically inflated to a pressure that is less than the inflated pressure of the inflatable tubes 44A, 44B. As a result, the base 42 easily conforms to the contours of the patient P because of the patient's weight. More specifically, the weight of the patient P causes the base 42 to assume a bowl-shape that is tailored to the patient's body (FIG. 3). The base 42 and inflatable tubes 44A, 44B can be inflated manually or with an air pump. It is to be understood that the compliant support 24 may have different shapes and sizes or be conformable with the patient's body in a way different from that described herein.

Figure 8:
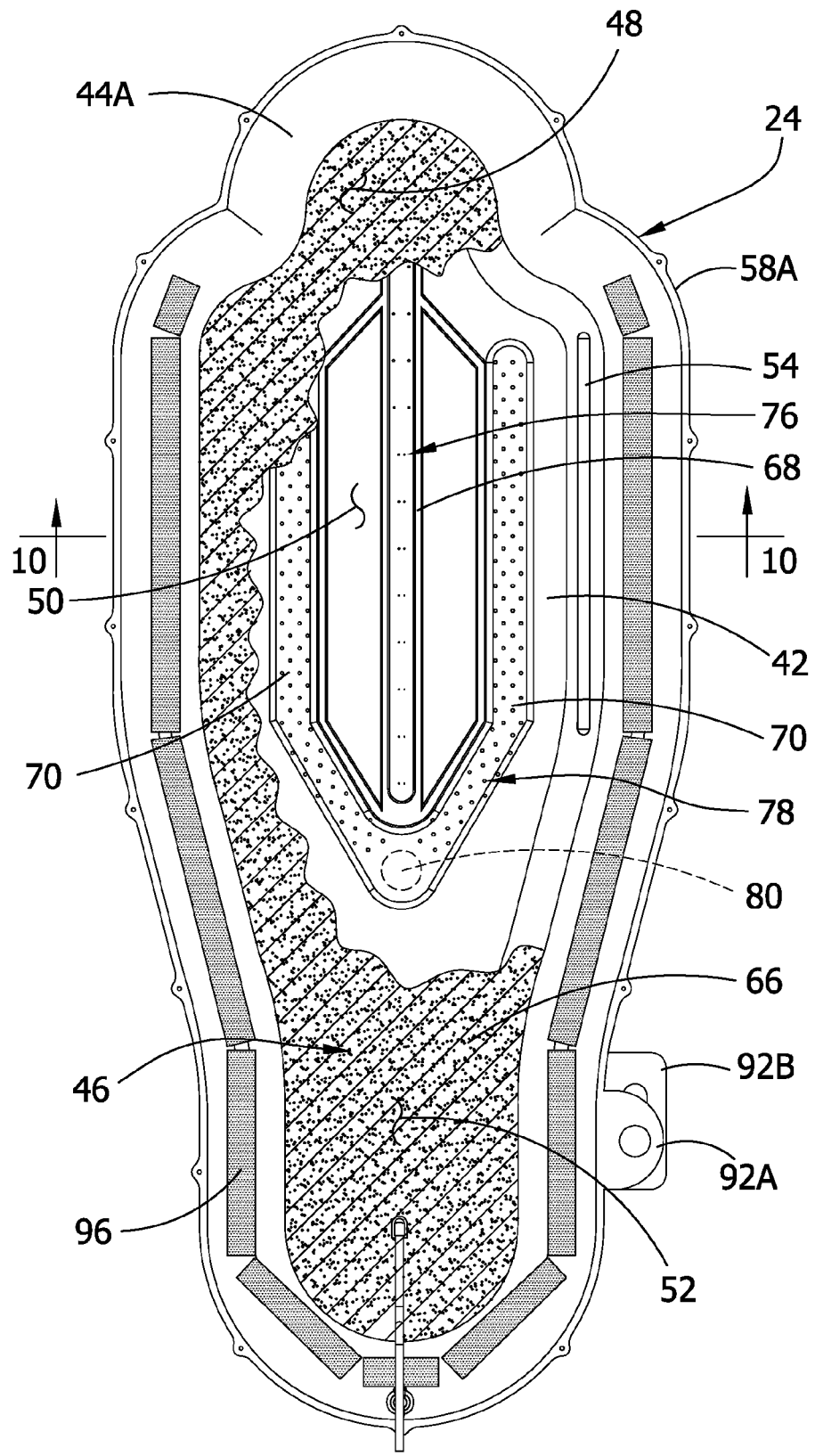
FIG. 8 is a top plan of a compliant support of the enclosure with parts broken away to show internal construction.

With reference to FIG. 8, the well 46 comprises a pocket 48 sized and shaped for receiving the head and neck of the patient P, a broader region 50 for receiving the torso of the patient, and a tapered pocket 52 for receiving the legs and feet of the patient. The pocket 48, which is adapted for receiving the head and neck of the patient P, is configured to support the head in an upward-facing direction thereby maintaining the patient's breathing passageways (i.e., nose and mouth) out of contact with the heat transfer liquid 18. The pocket 48 prevents the head of the patient P from moving to a side-facing direction and holds the head of the patient at a relatively higher position than the torso of the patient. It is to be understood that a head rest (not shown) can be used to support the patient's head. The head rest can be formed as one-piece with the compliant support 24 or provided separately.

The broader region 50 of the well 46 further includes a pair of shoulder gussets 54 for receiving the shoulders of the patient P. The shoulder gussets 54 allow the base 42 to expand in the shoulder region of the patient P, which is often the broadest region of the patient, to accommodate patients with varying shoulder widths.

As illustrated in FIG. 3, the well 46 is deeper in the broader region 50 receiving the torso of the patient P than in the pocket 48 receiving the head or the tapered pocket 52 receiving the legs and feet since a large portion of the patient's weight is contained in the torso. More specifically, the well 46 has a depth D in the broader region 50 adapted to receive the torso between about 2.5 centimeters (1 inch) and about 20 centimeters (8 inches), and preferably between about 10.2 centimeters (4 inches) and about 15 centimeters (6 inches), which correspond generally to about one-half of the chest heights of adult males between the 5th percentile and 95th percentile.

The variation in depths in the well 46 allows more heat transfer liquid 18 to accumulate around the torso of the patient P, a region of the body amenable to heat transfer, than around the head, legs, and feet of the patient P. The reasons for managing the depth of the heat transfer liquid 18 in the pocket 48 adapted to receive the head of the patient P are apparent and explained previously herein. It is to be understood that the well 46 can have a generally uniform depth D or have depths different from those indicated without departing from the scope of this invention. For example, an enclosure designed for use with smaller adults, children, or babies, would have depths less than those disclosed herein.

Figure 9:
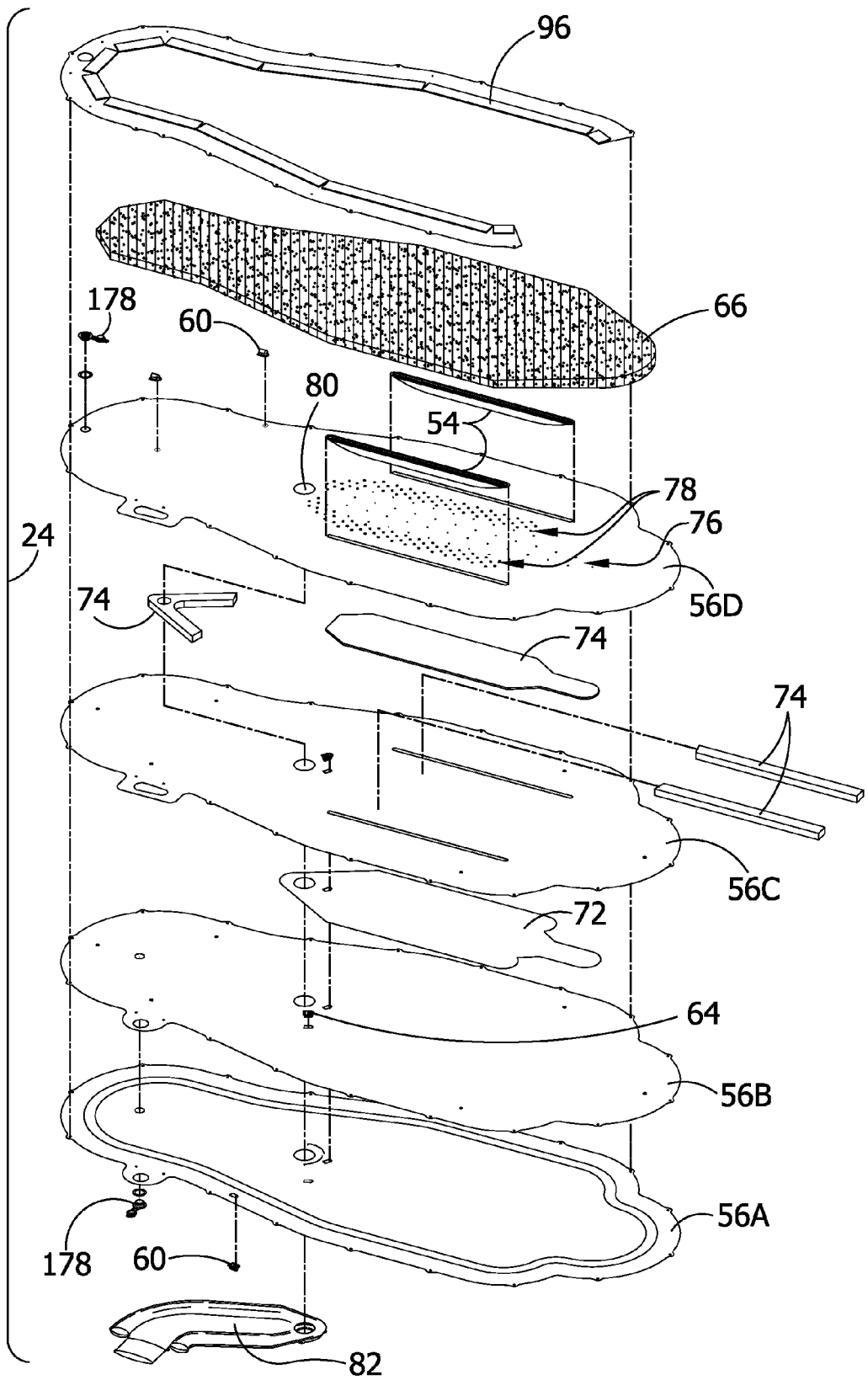
FIG. 9 is an exploded perspective of the compliant support.
Figure 10:
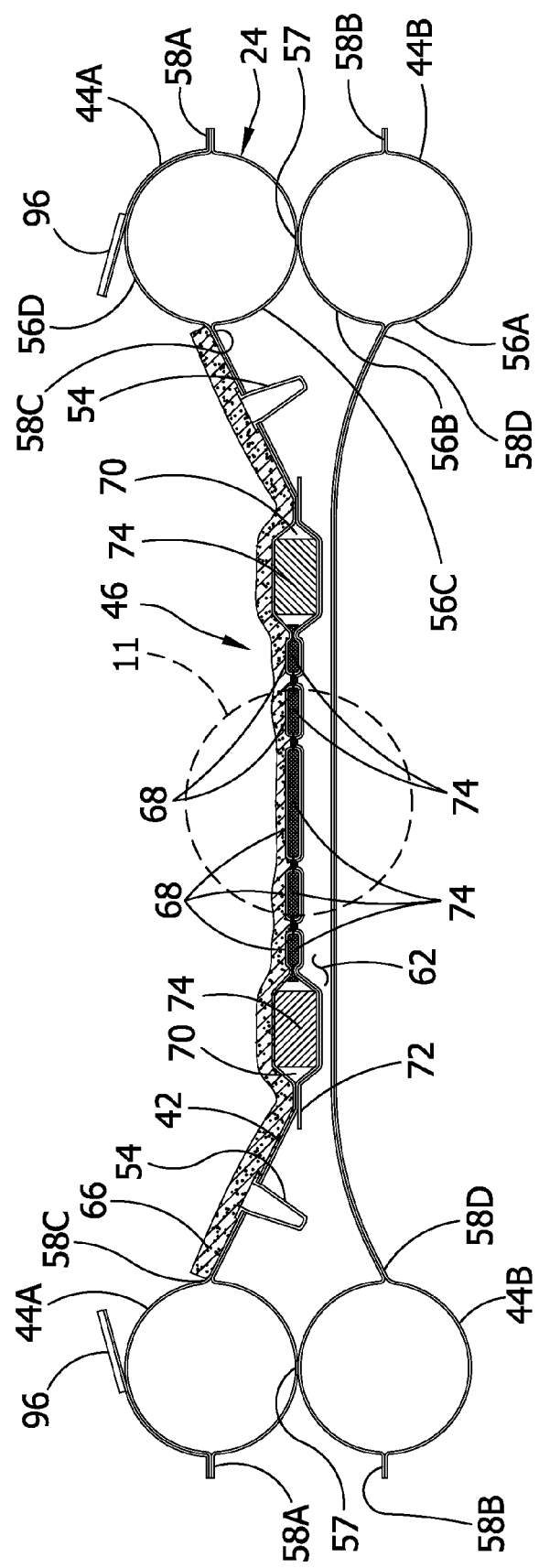
FIG. 10 is a section on line 10-10 of FIG. 8.

With reference to FIGS. 9 and 10, the illustrated compliant support 24 is formed using four flexible sheet-like components. As illustrated, a first component 56A and a second component 56B are paired together, and a third component 56C and a fourth component 56D are paired together. The paired components 56A, 56B and 56C, 56D are placed in face-to-face engagement with one another and joined at first seals 58A, 58B that extend around the peripheries thereof and at second seals 58C, 58D that are spaced inward from the peripheries. The portions of the components 56A-D located between the first seals 58A, 58B and the second seal 58C, 58D cooperatively define the inflatable tubes 44A, 44B. Particularly, the paired first and second components 56A, 56B form the lower tube 44B, and the paired third and fourth components 56C, 56D form the upper tube 44A. Referring again to FIG. 9, a respective doghouse connector 60 extends into each of the portions of the components 56A-D located between the first seals 58A, 58B and the second seals 58C, 58D for allowing the inflatable tubes 44A, 44B to be inflated using an exterior air source (i.e., manually or an air pump).

The paired first and second components 56A, 56B forming the lower tube 44B are overlaid by the paired third and fourth components 56C, 56D forming the upper tube 44A and sealed together. More specifically and with reference to FIG. 10, the third component 56C is sealed to the second component 56B along a continuous seal 57 to define a sealed chamber 62 that is formed between the joined first and second components 56A, 56B and the joined third and fourth components 56C, 56D. The sealed chamber 62 is inflatable and, when inflated, underlies and provides support for the patient P received in the well 46. A doghouse connector 64 extends into the sealed chamber 62 for allowing air to be introduced into the sealed chamber 62 to thereby inflate the base 42 using a suitable exterior air source.

A porous layer 66 is used to cover the well 46 so that the porous layer is disposed between the body of the patient P and the fourth component 56D (FIGS. 3 and 10). The porous layer 66, such as rich loft polyester batting or open-cell polyurethane foam, allows heat transfer liquid 18 to flow between the body of the patient P and the well 46 and thereby across the skin of the patient. The porous layer 66 prevents areas of the well 46 from being sealed off from the body of the patient P contacting the fourth component 56D, which would inhibit flow of heat transfer liquid 18 beneath the body of the patient.

Figure 11:
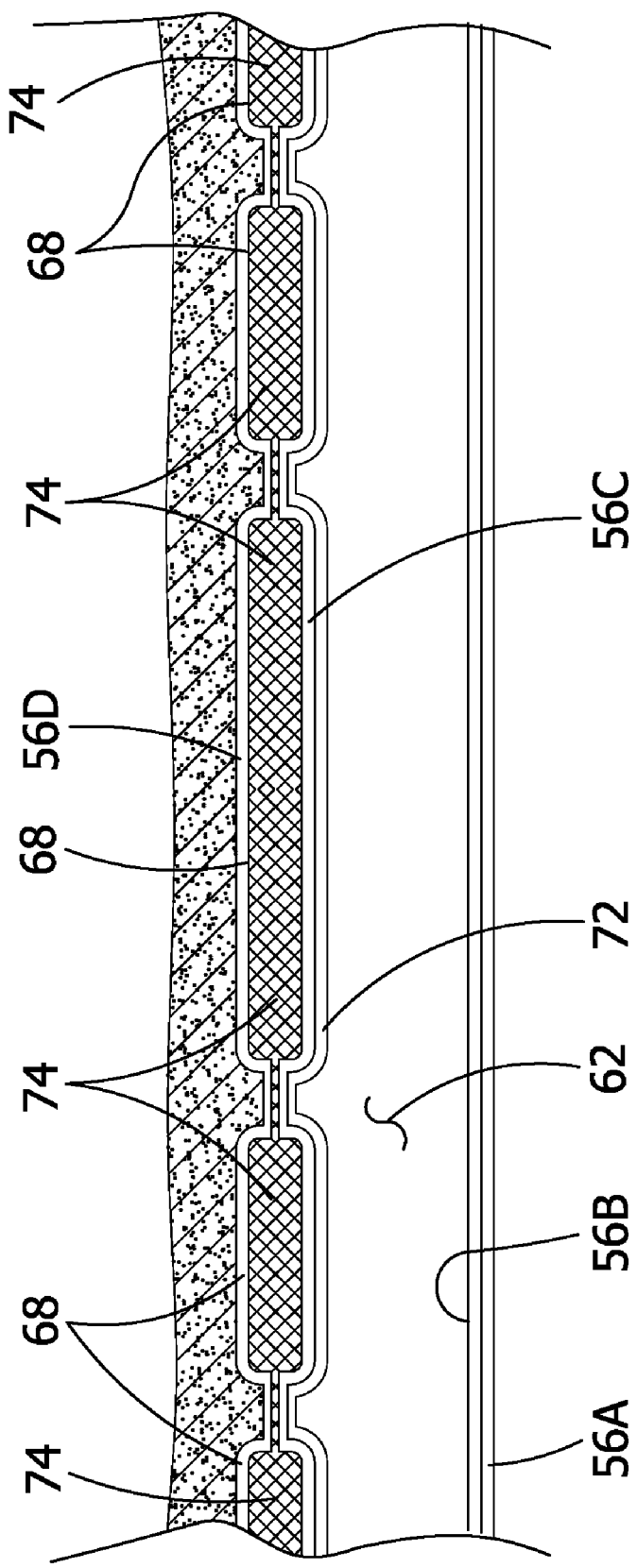
FIG. 11 is an enlarged fragment of the compliant support shown in FIG. 10.

With reference to FIGS. 8, 10, and 11, the third and forth components 56C, 56D also cooperatively define a plurality of supply passages 68 for allowing heat transfer liquid 18 to be supplied beneath the body of the patient P, and two return passages 70 for allowing heat transfer liquid to be drained from the well 46. The illustrated supply and return passages 68, 70 are formed using heat sealing but it is to be understood that other methods of forming the passages 68, 70 or sealing the components 56C, 56D to one another, such as adhesives, can be used. The passages 68, 70 have a length approximately equal to the about half the length of the compliant support 24 and are generally located in the broader region 50 of the well 46.

Since the return passages 70 rely on gravity for fluid flow, the return passages are substantially larger in cross-section than the supply passages 68 (FIG. 11). The supply passages 68 can be sized smaller since a pump is used to drive heat transfer liquid 18 into the passages. A reinforcing layer 72 is attached to the third component 56C beneath the passages 68, 70 to provide additional structural integrity to the passages. It is to be understood that the number, location, and dimensions provided herein for the passages 68, 70 are exemplary only and that more or fewer passages can be formed and that the passages can be formed to have various dimensions, various location on the compliant support.

Referring now to FIGS. 10 and 11, each of the passages 68, 70 formed in the compliant support 24 are supported by a hold-open 74, which holds the passages open and permits flow of the heat transfer liquid 18 through the passage past the hold-open. The hold-opens 74 provide the rigidity necessary to maintain the passages 68, 70 open even when subjected to a load, such as the weight of the body of the patient P which bears on the passages formed in the well 46. The hold-open 74 may be a porous material, such as open-celled foams, particulate matter (e.g., polystyrene beads), batting, non-woven materials, or mechanical devices, such as coil springs. One suitable open-celled foam is a reticulated polyurethane foam having approximately 25 pores per inch manufactured by Foamex of Eddystown, Pa., USA, and sold under the trade name SIF®.

With reference again to FIGS. 8 and 9, the fourth component 56D of the compliant support 24 has a plurality of openings 76 (i.e., inlets) therein corresponding to the supply passages 68 for allowing the heat transfer liquid 18 to pass from the passage into direct fluid contact with the underside of the patient's body received in the well 46. Each of the illustrated openings 76 is generally circular and has a diameter of about 1 millimeter (0.04 inches). The openings 76 are enlarged in the accompanying figures so that they can be seen. The small diameter openings 76 restrict the flow of heat transfer liquid 18 from the passage 68 into the enclosure 14 thereby causing the entire lengths of the passages to fill with heat transfer liquid and evenly distributing the heat transfer liquid along the lengths of the passages.

The forth component 56D also has a plurality of larger sized apertures 78 (i.e., outlets) therein corresponding to the return passages 70 for allowing heat transfer liquid 18 to exit the well 46. The return passages 70 and the well 46 of the compliant support 24 are fluidly connected to at least one large diameter (e.g., 2.5 centimeters (1 inch)) outlet 80 extending through all four of the sheet-like components 56A-D for draining heat transfer liquid 18 from the well. It is contemplated that the large diameter outlet 80 may be larger or smaller than 2.5 centimeters. The illustrated outlet 80 is preferably sufficiently sized to allow heat transfer liquid 18 to be drained from the well 46 by gravity at a rate equal to or greater than the rate at which the heat transfer liquid is being delivered to the interior space 16 of the enclosure 14 to prevent the enclosure from overflowing. Moreover, the illustrated large diameter outlet 80 is located in the broader region 50 of the well 46, which is adapted to receive the torso of the patient P. As indicated above, the broader region 50 is typically the deepest portion of the well 46 or, in other words, the lowest portion of the well. As a result, large diameter outlet 80 is located in what is typically the lowest portion of the well 46. The well 46 may have more than one outlet 80, the outlet may be positioned at other sections of the enclosure, and the outlet may have other sizes and shapes.

Figure 12:
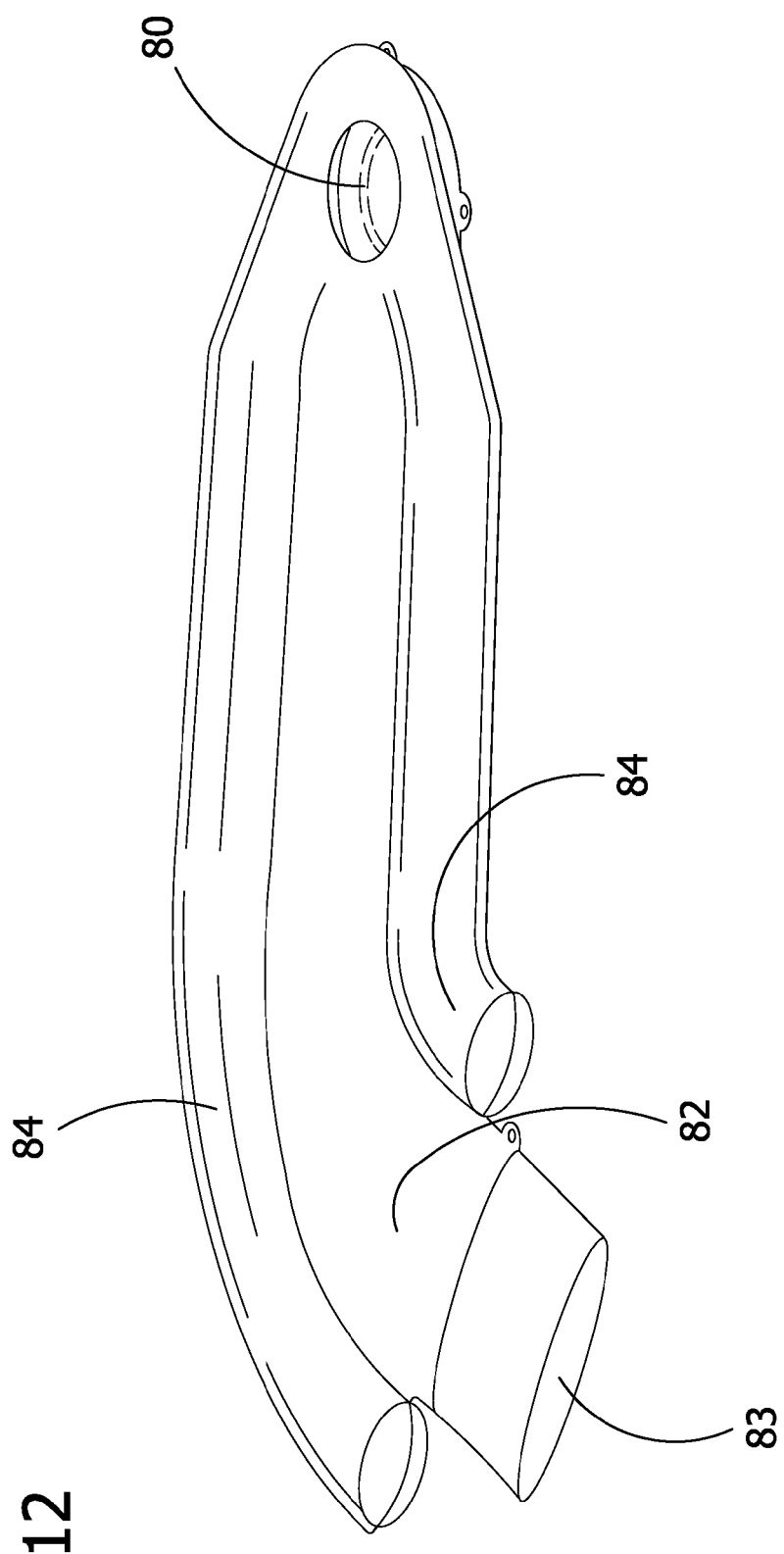
FIG. 12 is a perspective of a drain tube for the compliant support.

Referring to FIGS. 9 and 12, a drain tube 82 is fluidly connected to the large diameter outlet 80 for transferring heat transfer liquid 18 away from the interior space 16 of the enclosure 14. At least a portion of the drain tube 82 is located underneath the compliant support 24. As a result, the drain tube 82 is provided with at least one hold-open 84 to keep the drain open during use of the apparatus 10. In the illustrated configuration, the hold-open 84 for the drain tube 82 are two, elongate inflatable tubes that flank the sides of the drain. One of the elongate inflatable tubes is located adjacent one side of the drain tube 82 and the other inflatable tube is located adjacent the opposite side of the drain tube. It is to be understood that other types of hold-opens 84, including those described above, could be used or that the drain tube 82 could be formed from material with sufficient rigidity as to not warrant the use of the hold-open.

With reference now to FIGS. 1 and 13-16, a weir 86 (broadly, "a flow restrictor") is in fluid communication with the drain tube 82 and the large diameter outlet 80 for maintaining the depth D of the heat transfer liquid 18 within the well 46 at a predetermined level thereby allowing the heat transfer liquid to accumulate in the well adjacent and beneath the patient P. Specifically, a drain tube outlet 83 is attached to a weir inlet 85 so that heat transfer liquid flowing from the interior space 16 of the enclosure 14 flows through the drain tube 82 and into the weir 86. It is to be understood that the flow restrictor may be a device besides the weir 86, such as an inverted U-shaped tube or an adjustable valve, without departing from the scope of this invention.

Figure 13:
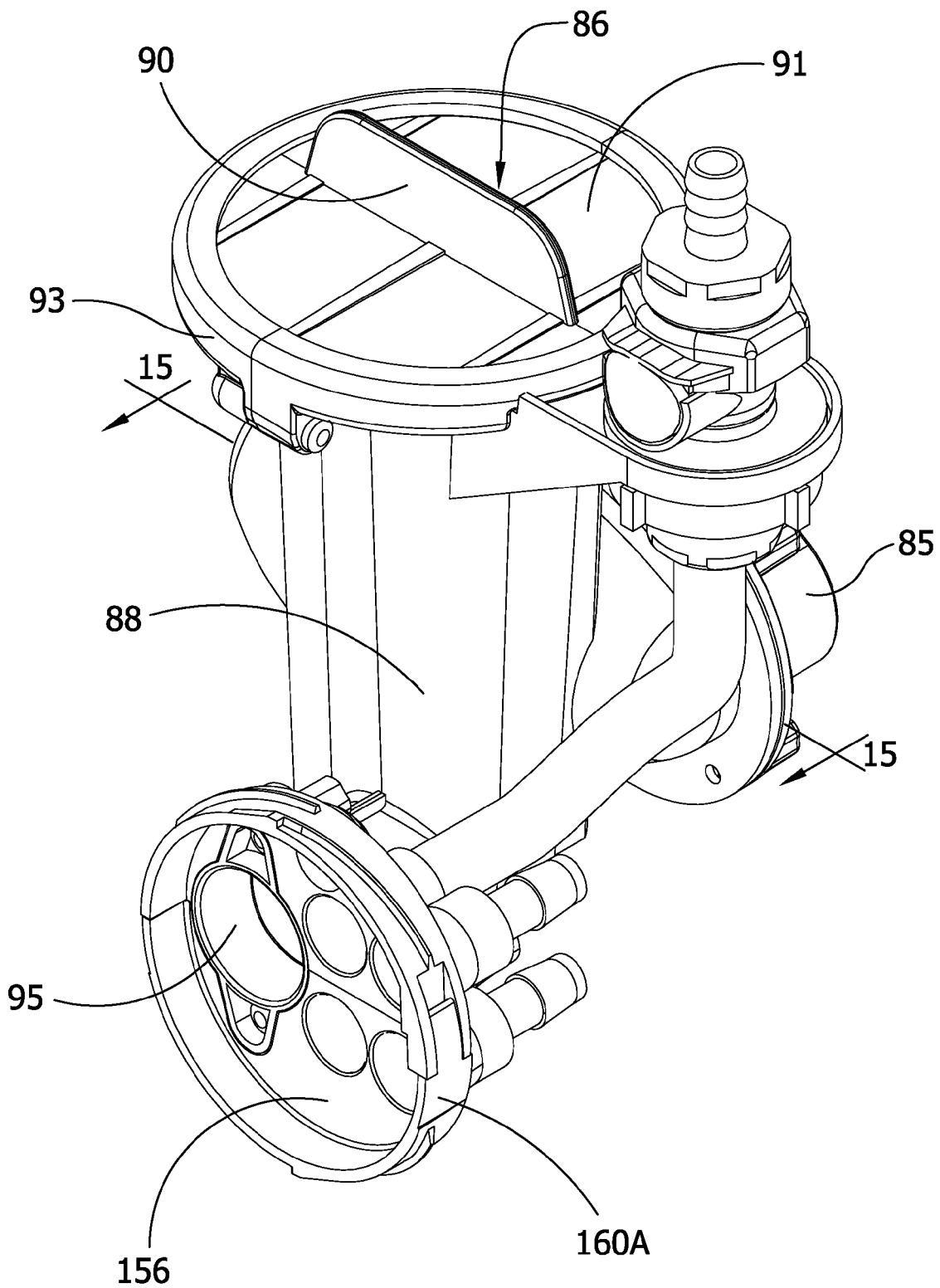
FIG. 13 is a perspective of a housing for a weir.

The weir 86 includes a dam 87 of a predetermined height which the heat transfer liquid 18 must flow over before it is drained from the enclosure 14 (FIG. 13). For instance, if the heat transfer liquid 18 is maintained at a depth of between about 7 centimeters (2.8 inches) and about 15 centimeters (6 inches) in the well 46, the weir 86 needs to have a height H sufficient to prevent heat transfer liquid below the selected height from flowing out of the well. Since the weir 86 maintains heat transfer liquid 18 at a given depth D in the well 46, the weir creates a positive gage pressure as measured at the large diameter outlet 80, which would between about 0.69 kilopascals (0.1 pounds per square inch) and about 1.47 kilopascals (0.2 pounds per square inch) for the well 46 with a depth of heat transfer liquid between 7 centimeters (2.8 inches) and about 15 centimeters (6 inches).

Figure 14:
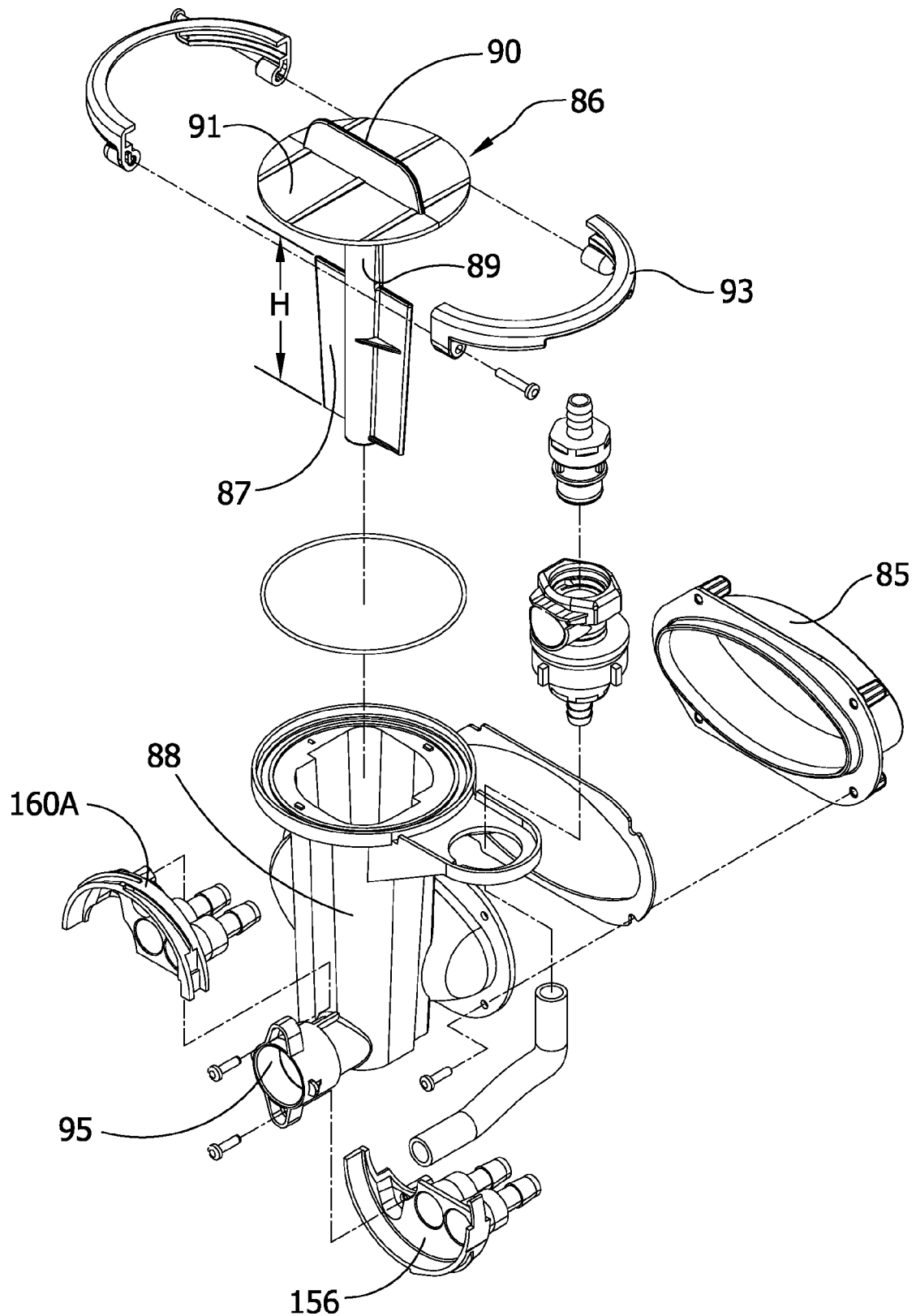
FIG. 14 is an exploded perspective of the housing.
Figure 15:
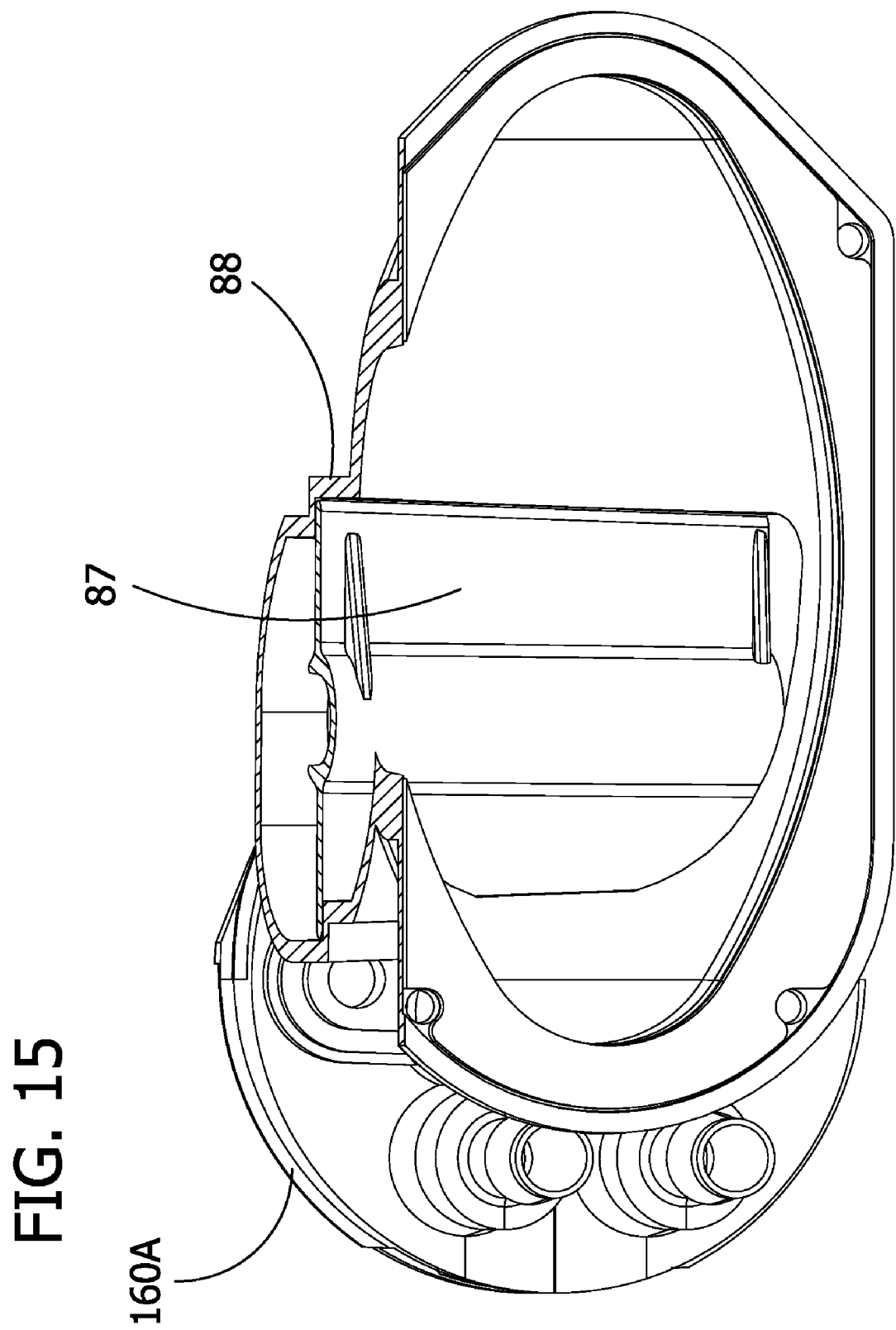
FIG. 15 is a section on line 15-15 of FIG. 13 showing the weir in a flow restricting position.

The weir dam 87 is located in a weir housing 88 and cooperates with the housing 88 to selectively retard the flow of heat transfer liquid 18. As illustrated in FIG. 14, the weir dam 87 comprises a generally rectangular web affixed to shaft 89. A cap 91 of the weir housing 88 is also affixed to the shaft 89 but is spaced from the weir dam 87. The cap 91 is rotatably secured to the weir housing using a clamp 93. The cap 91 includes a handle 90 for rotating the cap 91 and thus, the shaft 89 and weir dam 87 with respect to the housing 88.

The handle 90 can be used to selectively move the weir 86 between a flow restricting position (FIG. 15) wherein the weir dam 87 creates a spillway which the heat transfer liquid 18 must flow over before it is exhausted from the well 46, and a non-restricting position (FIG. 16) wherein the weir dam is rotated and substantially allows the heat transfer liquid to flow unimpeded from the well. The non-restricting position of the weir 86 is used to rapidly purge the interior space 16 of the enclosure 14 of heat transfer liquid 18. A weir outlet 95 allows heat transfer liquid 18 that has passed over the weir dam 87 to exit the weir housing 88. It is to be understood that the flow restrictor could be automatically moved between the restricting position and non-restricting position using a controller, which is described below.

As illustrated in FIG. 1, the weir housing 88 is secured by an upper support 92A and a lower support 92B integrally formed with the compliant support 24. The upper and lower supports 92A, 92B are adapted to hold the weir housing 88 and thereby the weir 86 in proper alignment with respect the compliant support 24.

As shown in FIGS. 1 and 2, the cover 22 and the compliant support 24 are adapted for engagement with each other. The cover 22 includes a first sealing portion 94 (FIG. 4) and the support 24 includes a second sealing portion 96 (FIG. 8) for engaging with the first sealing portion 94. The sealing portions 94, 96 allow the cover 22 to be completely or partially removed from compliant support 24. In the illustrated embodiment, the sealing portions 94, 96 comprise a hook and loop fastening system. For example, a strip of hook material is shown adhered to the compliant support 24, and a strip of loop material is shown adhered to the cover 22 for engaging the hook material located on the compliant support. It is to be understood that the loop material can be placed on the compliant support 24 and the hook material on the cover 22. It is also understood that other types of fastening systems (e.g., adhesives, slide fasteners, snaps) can be used. It is further understood that a portion of the cover 22 can be bonded to the compliant support 24 to thereby hingedly attach the cover to the compliant support.

The cover 22 is slightly smaller than the support 24 which allows the sealing portions 94, 96 of both the cover and the compliant support to lie above and laterally inward from the sides of the support. As a result, the sealing portions 94, 96 are positioned away from the medial line of the patient P received in the interior space 16 of the enclosure 14 thereby allowing CPR to be administered to the patient without interference from the sealing portions.

Furthermore, the sealing portions 94, 96 are positioned on a portion of the enclosure 14 that is maintained generally horizontal. As a result, the potential for the sealing portions 94, 96 to be bent or otherwise deformed is minimized. Bending and deformation of the sealing portions 94, 96 may diminish the ability to seal or to be opened or closed. Moreover, the sealing portions 94, 96 are positioned at a location above the depth D at which heat transfer liquid 18 accumulated in the well 46 of the compliant support 24, which reduces the demand on the sealing portions (i.e., the sealing portions do not have to form water tight seals). Lastly, the sealing portions 94, 96 are conveniently located for a user thereby providing the user with easy access to the patient P.

Figure 24:
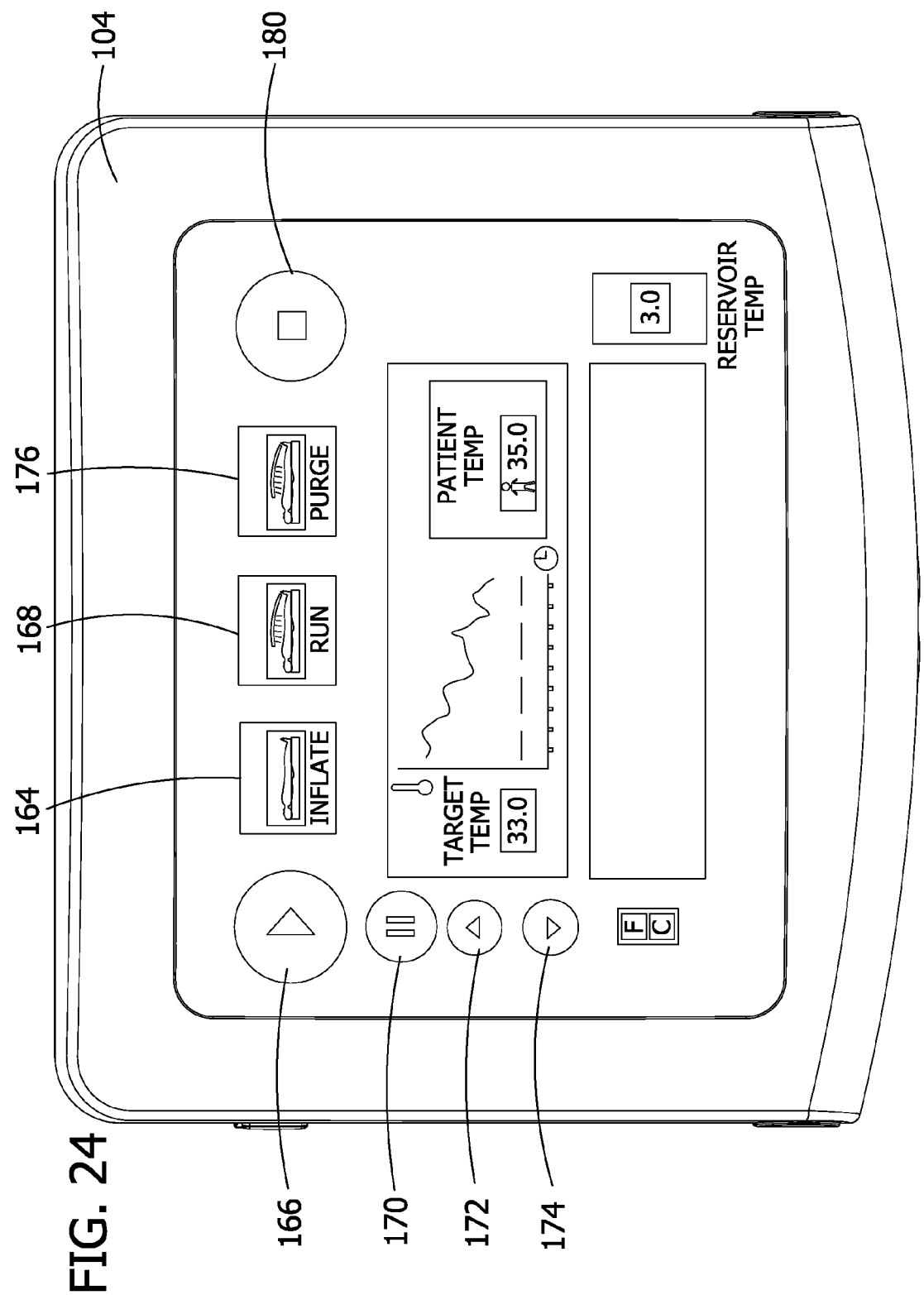
FIG. 24 is a plan view of a monitor of the mobile cart displaying a user interface for the control system.
Figure 25:
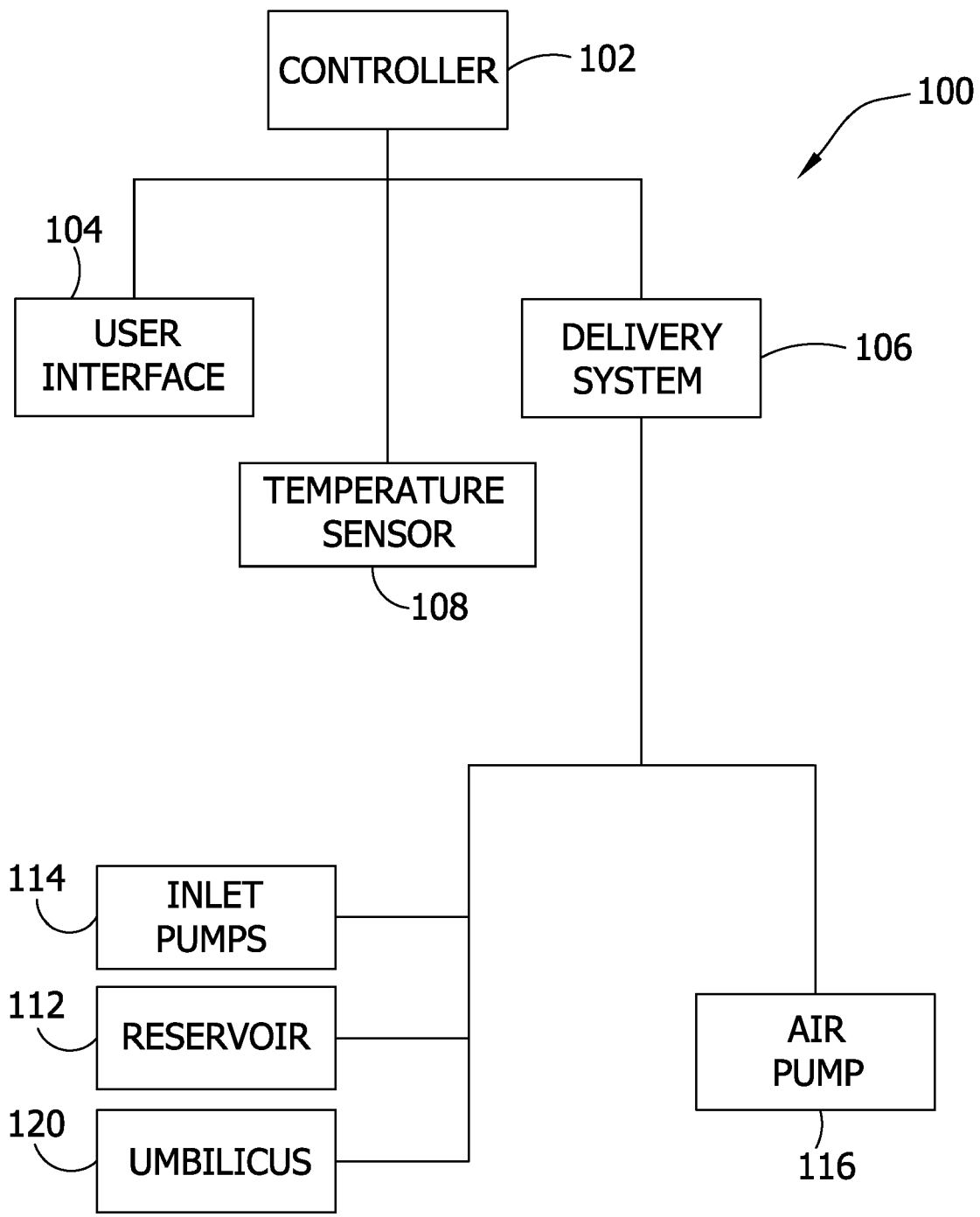
FIG. 25 is a schematic of the control system.

Referring now to FIGS. 1, 17-19, and 25, the apparatus 10 further comprises a control system, generally indicated at 100, for controlling operation of the apparatus 10. The control system 100, which is mounted on a mobile cart 98, includes a controller 102, a monitor 104 (broadly, a "user interface"), a delivery system, and a temperature sensor 108 for measuring the temperature of the patient P. The monitor 104 includes a LCD touch screen display for visually indicating particular parameters of the control system 100 and for allowing the user of the system to selectively control particular system functions (FIG. 24). The monitor 104, for example, could display a target temperature along with the actual body temperature of the patient P, and the temperature of the heat transfer liquid 18, among other things. With respect to user control of the system 100, the user can start, pause, and stop the delivery system using the touch screen display of the monitor 104. It is also understood that other system 100 functions could be controlled by the user using the touch screen display of the monitor 104.

The delivery system of the control system 100 comprises the liquid delivery system and a gas delivery system. The liquid delivery system is a generally closed, continuous flow system in which heat transfer liquid 18 is cycled through the interior space 16 of the enclosure 14. The liquid delivery system comprises a fluid reservoir 112, two liquid inlet pumps, generally indicated at 114, with disposable gear pumpheads contained within a housing 140 driven by motorized drive gears 115, and an umbilicus 120. The umbilicus 120 fluidly connects the reservoir 112 and two liquid pumps 114 to the interior space 16 of the enclosure 14. It is to be understood that the delivery system can have fewer or more components without departing from the scope of this invention.

The reservoir 112 holds heat transfer liquid 18 before the pumps 114 pump the heat transfer liquid into the interior space 16 of the enclosure 14. The reservoir 112 may have insulation (not shown) to help maintain the temperature of the heat transfer liquid 18 before it is pumped into the enclosure 14. Although various sized reservoirs may be used, the reservoir 112 in the illustrated embodiment has a capacity sufficient to hold about 30 liters (about 8 gallons) of heat transfer liquid 18. It is to be understood that reservoirs having different capacities may be used. For example, a reservoir for holding heat transfer liquid for the child or baby sized enclosure may have a smaller capacity where as a reservoir for holding heat transfer liquid for a larger enclosure may have a larger capacity.

Figure 17:
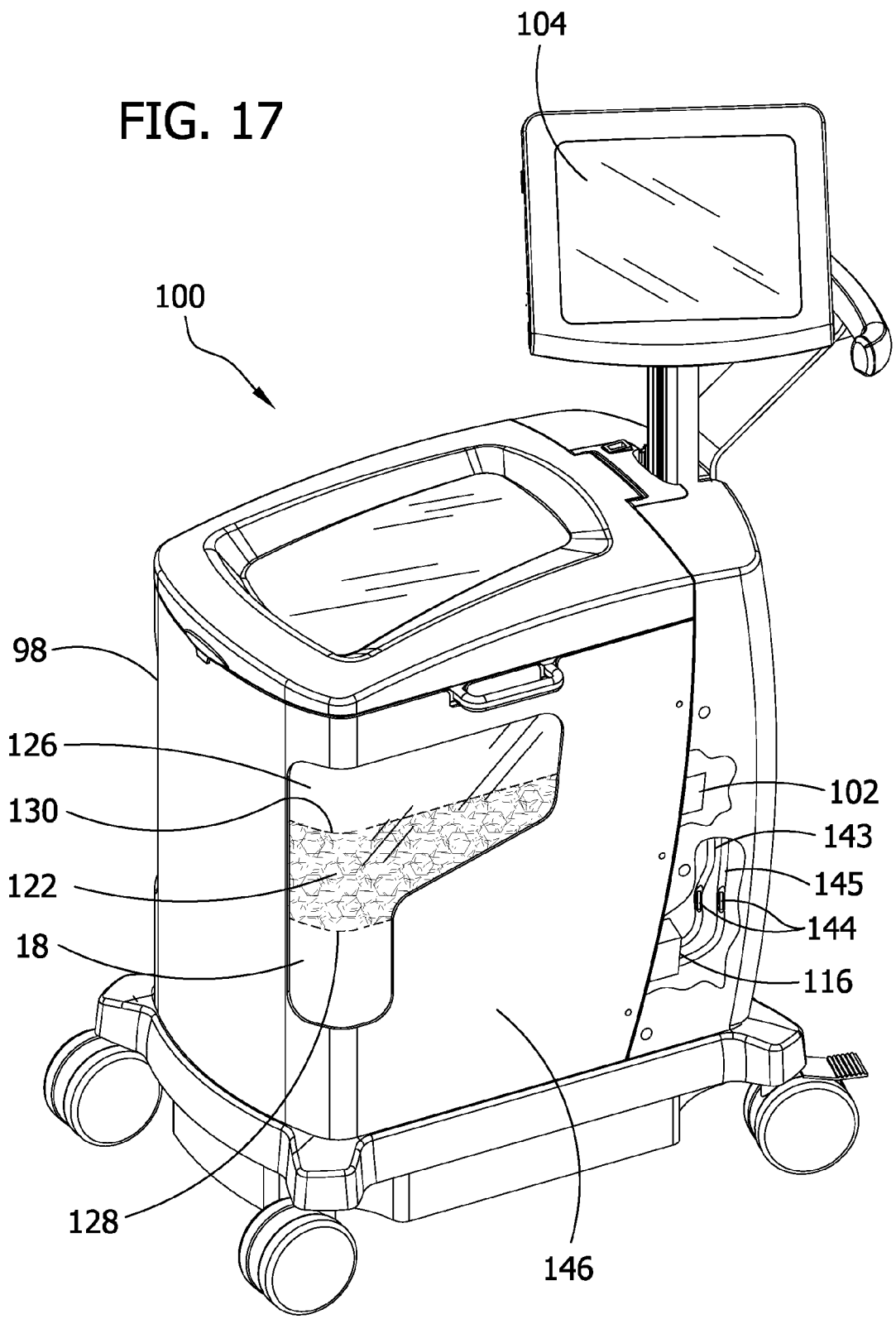
FIG. 17 is a perspective of a mobile cart housing a control system with portions of the cart broken away to show an air pump and a controller of the control system.

A phase change material 122 (e.g., ice) is also placed into the reservoir 112 to alter and/or maintain the temperature of the heat transfer liquid 18 to an inlet temperature, measured before the liquid enters the enclosure 14 (FIG. 17). In the illustrated embodiment, approximately 10 liters (2.6 gallons) of ice 122 are placed into the reservoir 112 but other quantities of ice could be used. Moreover, additional ice 122 can be added to the reservoir 112, if necessary, during the operation of the apparatus 10 to maintain the heat transfer liquid 18 at the desired inlet temperature. Besides phase change materials 122, various other types of heat exchangers (e.g., Peltier device) are contemplated as being within the scope of the present invention.

Figure 19:
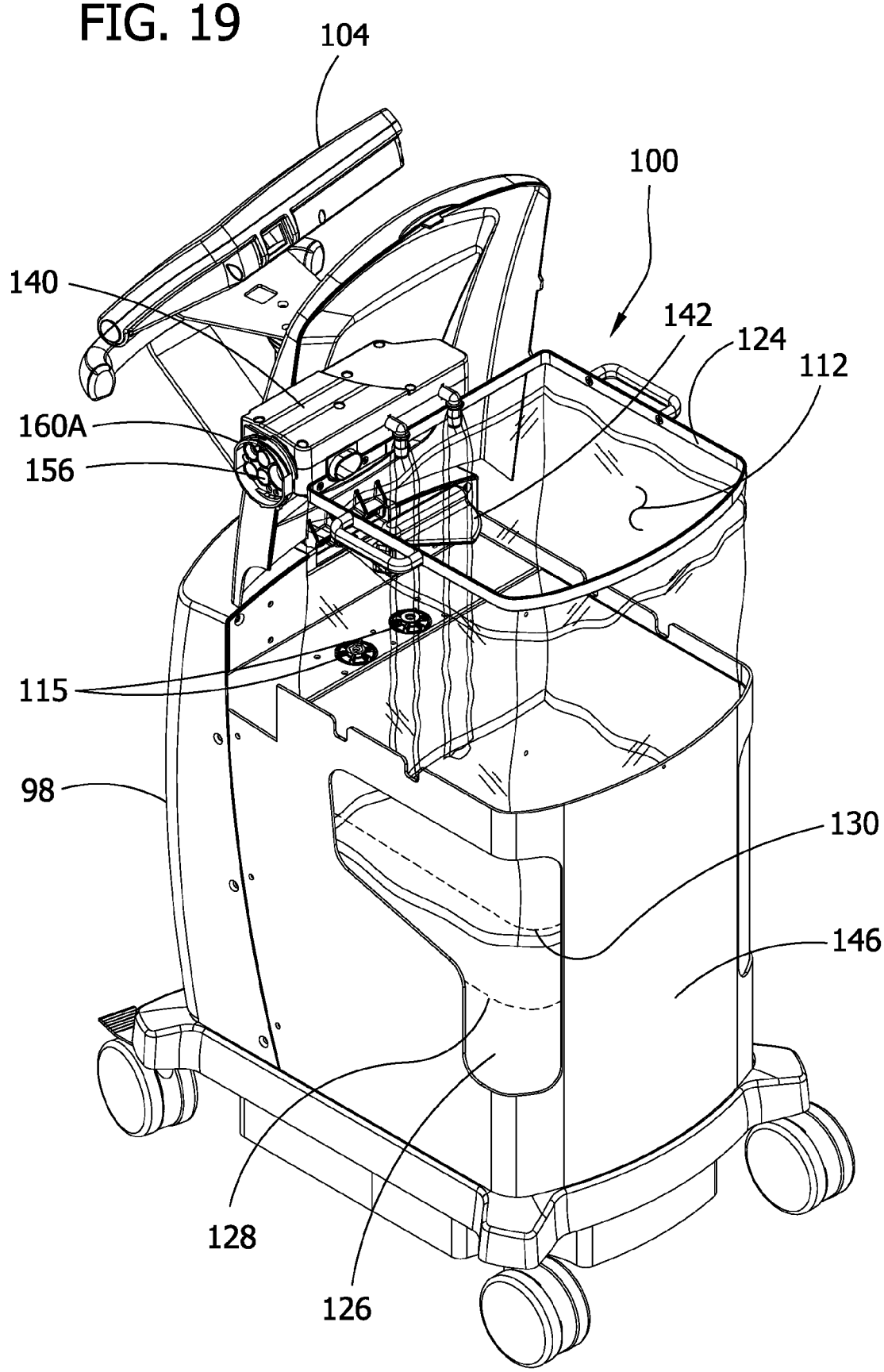
FIG. 19 is the perspective of FIG. 18 but showing a pump housing and a reservoir partially removed from the cart.

The illustrated reservoir 112 comprises a plastic bag removable supported in the mobile cart by a frame 124 with handles (FIG. 19). Moreover, the mobile cart includes a reservoir viewing window 126 for allowing the user to visually observe the ice 122 and heat transfer liquid 18 contained in the reservoir 112. The window 126 has a heat transfer fill line 128 to indicate the level to which heat transfer should be placed into the reservoir, and an ice and heat transfer fill line 130 to indicate the level to which ice 122 should be added to the heat transfer liquid in the reservoir. Ice 122 and heat transfer liquid 18 can be added to the reservoir 112, as necessary, during operation of the apparatus 10. It is contemplated that the ice 122 could be added to the reservoir 112 before heat transfer liquid 18. It is also contemplated the ice 122 and heat transfer liquid 18 could be pre-measured before placing them into the reservoir 112.

Figure 20:
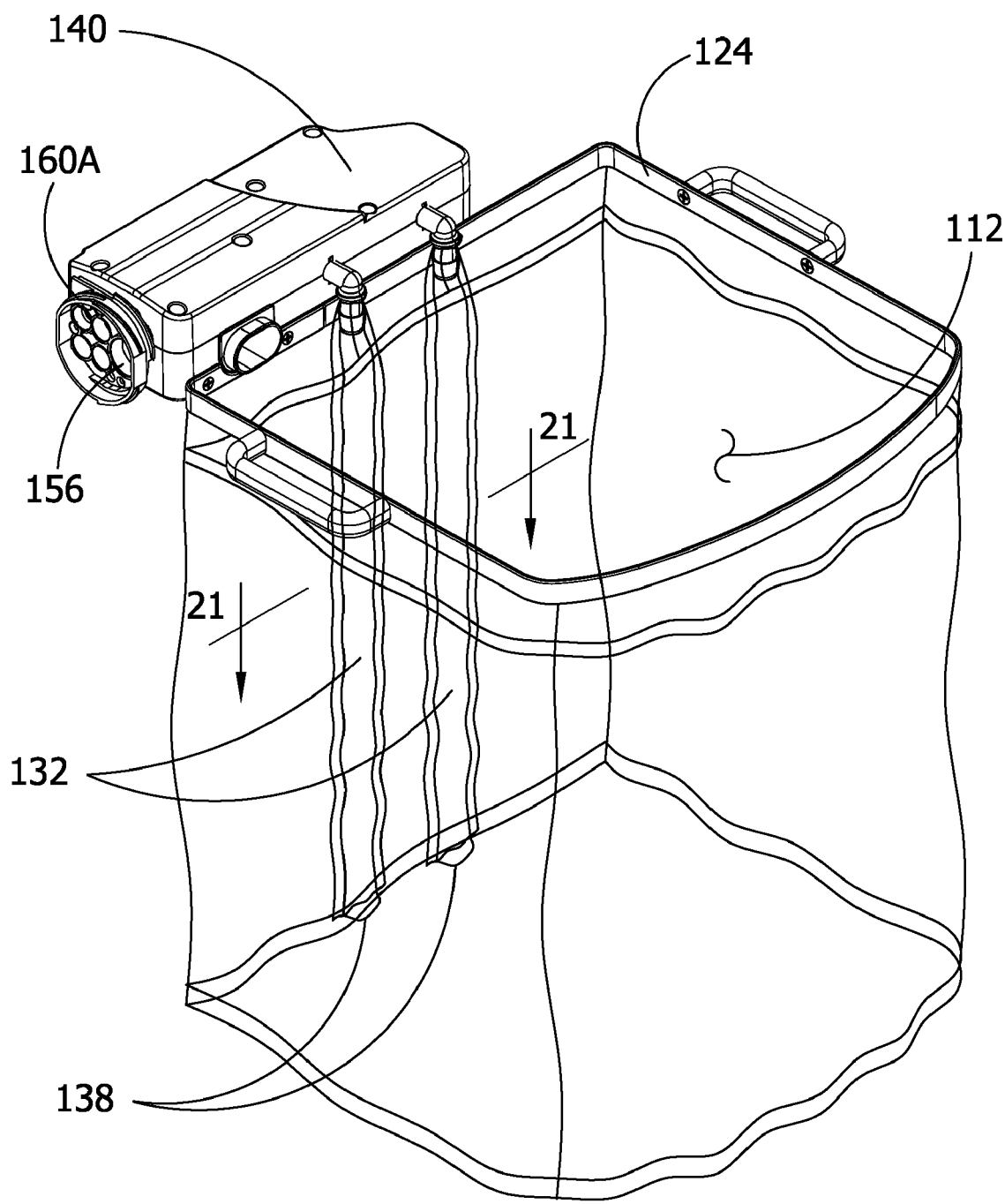
FIG. 20 is a perspective showing the pump housing and reservoir removed from the cart.
Figure 21:
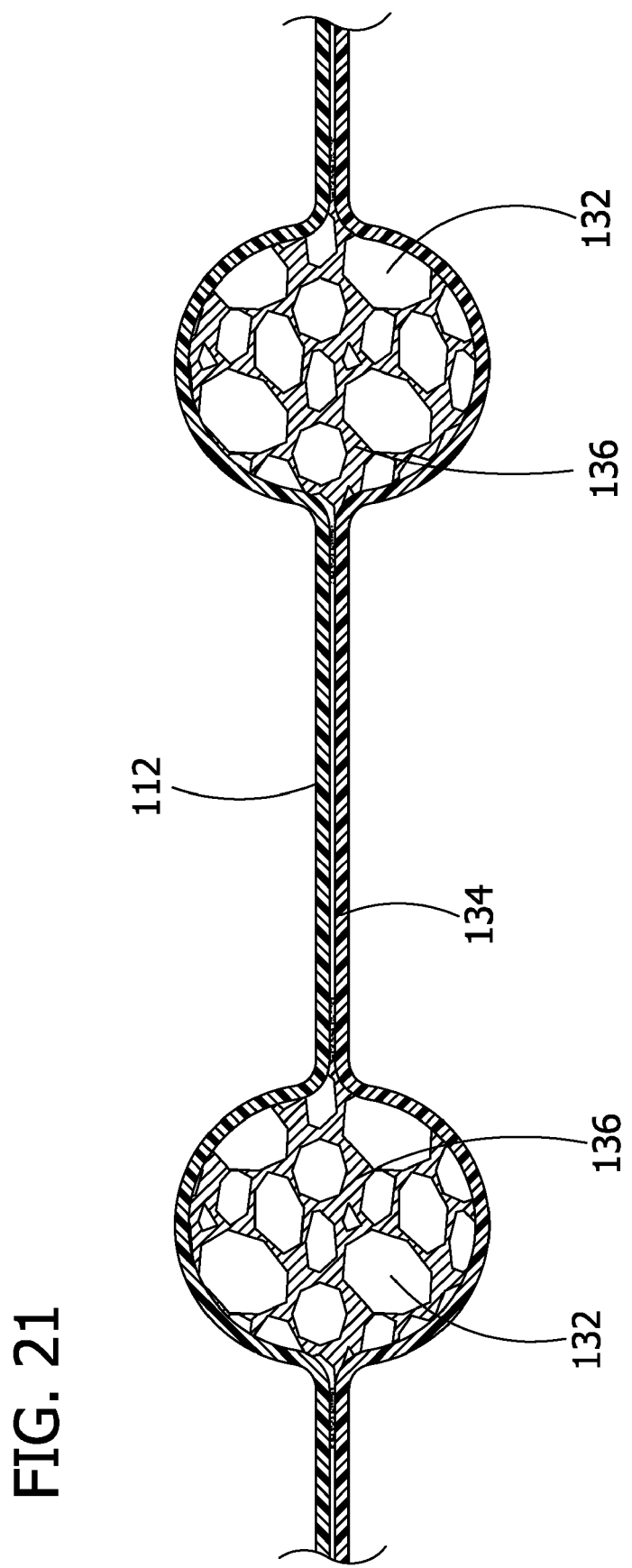
FIG. 21 is an enlarged, fragmentary section on line 21-21 of FIG. 20.

As illustrated in FIGS. 18-21, the reservoir 112 has two integrated passages 132 formed by heat sealing a separate sheet of material 134 to the bag. The passages 132 are used as intake passages for the pumps 114 (FIG. 19) for allowing the pumps to draw heat transfer liquid 18 from the reservoir 112 through the passages. The passages 132 include hold-opens 136 (as described above) to prevent the pumps 114 from drawing closed the passages during use (FIG. 21). The passages 132 have openings 138 adjacent the bottom of the reservoir 112, which prevents the buoyant ice 122 from being drawn into the pumps 114 while allowing the heat transfer liquid 18 to be drawn into the pumps (FIG. 20). It is to be understood that passages 132 can be formed separately from the reservoir 112 and could be formed from conventional polymeric tubing.

The two inlet pumps 114 are in fluid communication with the passages 132 formed in the reservoir 112, the umbilicus 120, and the passages 32, 68 in the enclosure 14 so that the pumps can pump heat transfer liquid 18 from the reservoir into the enclosure. More specifically, one of the pumps 114 directs heat transfer liquid 18 to the passages 32 in the cover 22 for directing heat transfer liquid 18 over the top of the body of the patient P, and the other inlet pump directs heat transfer liquid to the passages 68 in the compliant support 24 thereby directing heat transfer liquid underneath the patient's body.

Each of the pumps 114 can be operated independently of the other. Accordingly, heat transfer liquid 18 can be selectively directed for flow over the top of the body of the patient P, underneath the patient's body, or both (i.e., simultaneously over the top of the patient's body and underneath the patient's body). In the illustrated embodiment, one of the pumps 114 is capable of transferring liquid to the passages 32 in the cover 22 at a flow rate of about 8 liters per minute (2.1 gallons per minute). The other pump 114 is capable of directing heat transfer liquid 18 to the passages 68 in the compliant support 24 at a flow rate of about 6 liters per minute (1.6 gallons per minute). Thus, the two pumps 114 are capable of pumping heat transfer liquid 18 into the interior space 16 of the enclosure 14 at a flow rate of about 14 liters per minute (3.7 gallons per minute). It is to be understood that the pumps can have capacities other than those described herein and that a single pump or more pumps can be used to pump heat transfer liquid 18 into the interior space 14 of the enclosure 16.

The pumps 114 described above were specifically designed gear pumps for use in this apparatus 10 (FIG. 9). However, the pumps 114 can be conventional gear pumps, such as the UGP-2000 series manufactured by B&D Pumps, Inc. of Huntley, Ill., USA, or a roller-type pumphead with a motor drive, such as the 500 series process pump manufactured by Watson-Marlow OEM of Paramus, N.J., USA. Should higher flow rates or other parameters be required, alternative pumps, such as higher capacity gear or centrifugal pumps, may be used without departing from the scope of the present invention.

Figure 18:
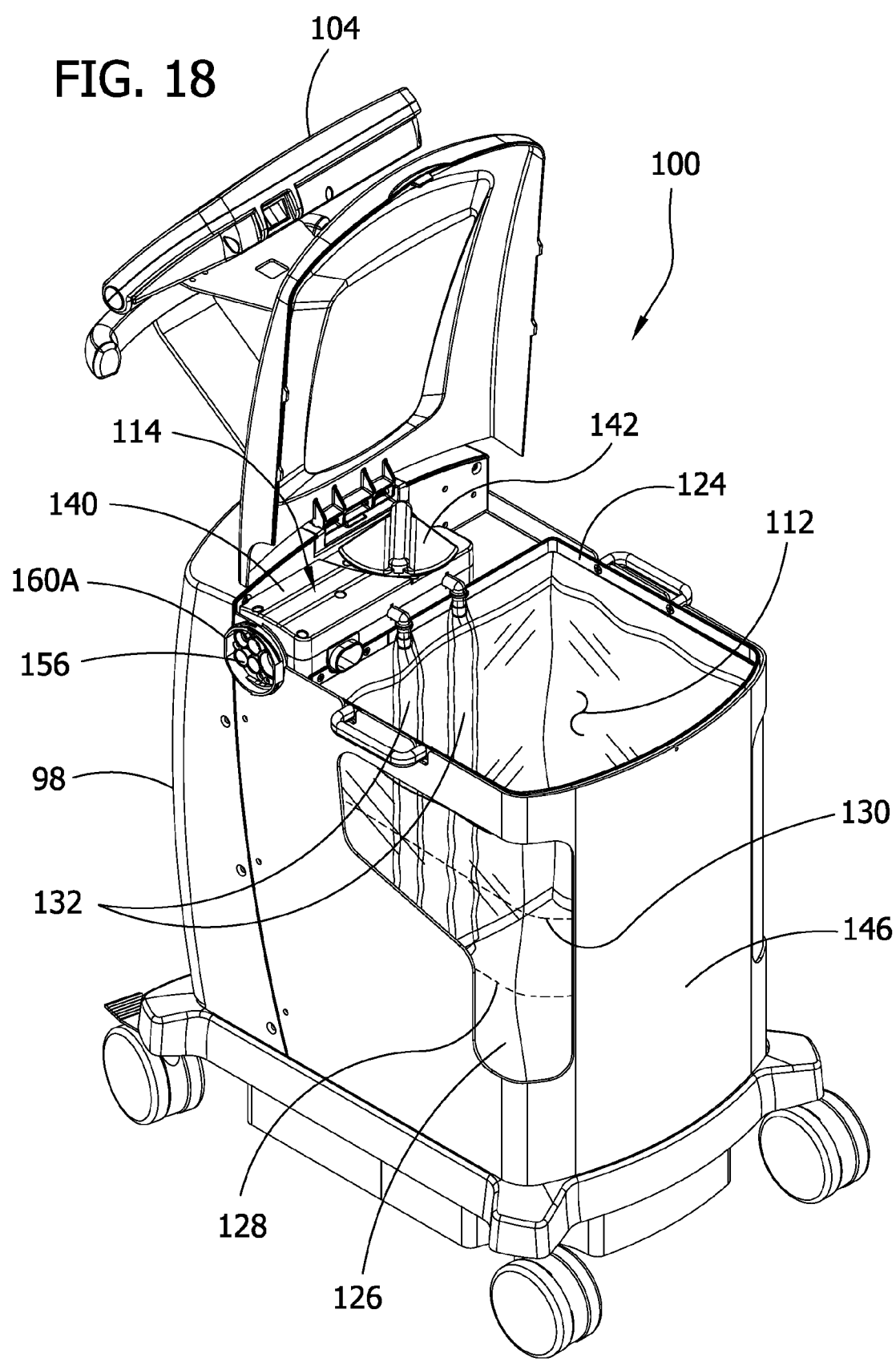
FIG. 18 is a perspective of the mobile cart showing a hinged lid of the cart opened.

Both of the pumps 114 incorporate detachable pumpheads (not shown) that are contained in the housing 140 (FIGS. 18-20). The housing 140 and thus, the pumpheads are disposable to minimize the likelihood of cross-contamination to subsequent patients. The pumpheads are the only part of the pumps 114 that contact the heat transfer liquid 18. In the illustrated embodiment, the pumphead housing 140 is held in place using a rotatable hold-down 142. As illustrated in FIG.

18, the hold-down 142 can be rotated to a position above the pumphead housing 140 thereby supporting the pumphead housing in position. As shown in FIG. 19, the hold-down 142 can be rotated so that the hold-down is clear of the pumphead housing 140 thereby allowing the pumphead housing and thereby the pumpheads to be removed from the pumps 114 and the mobile cart 98. Accordingly, after use, the pumpheads can be removed from the pumps 114, discarded properly, and a new pumpheads (i.e., a new pumphead housing 140) installed on the pump for use with the next patient.

The control system 100 further includes the gas delivery system for delivering pressurized air to inflate the various inflatable components of the compliant support 24. The gas delivery system comprises an air pump 116 and a plurality of pressure sensors 144 (FIG. 17). As shown, the air pump 116 and sensors 144 are located in a housing 146 of the mobile cart 98, and a portion of the housing 146 is shown broken away to expose the air pump and sensors. The air pump 116, such as a conventional reciprocating or scroll-type compressor, is in fluid communication with the compliant support 24 for inflating the inflatable tubes 44A, 44B, the sealed chamber 62, and the drain hold-opens 84. For example, the pump 116 may have the capacity to fill the inflatable tubes 44A, 44B of the compliant support 24 with air at a rate of about 500 liters per minute to a positive gauge pressure of about 3.4 kilopascals (0.5 pounds per square inch), the sealed chamber 62 to a positive gauge pressure of about 0.76 kilopascals (0.11 pounds per square inch), and the drain hold-opens 84 to a positive gauge pressure of about 3.4 kilopascals (0.5 pounds per square inch). It is to be understood that other types of air pumps can be used and that the air pumps can have different flow rates then those indicated.

The pressure sensors 144, which are shown in FIG. 17, are adapted to measure the air pressure within at least the inflatable tubes 44A, 44B and the sealed chamber 62 of the compliant support 24. In the illustrated configuration, one pressure sensor 144 is positioned within a first air line 143 that communicates with the inflatable tubes 44A, 44B and a second pressure sensor is positioned within a second air line 145 that communicates with the sealed chamber 62. But the gas delivery system could have more or fewer pressure sensors 144 without departing from the scope of this invention.

The pressure sensors 144 are connected to the controller 102 so that their air pressure measurements are conveyed to the controller so that the controller can compare the detected pressure measurements to predetermined pressures. The controller 102 is further connected to the air pump 116 so that if the detected measurements differ from the predetermined pressures, the controller can activate the pump to bring the air pressures within the inflatable tubes 44A, 44B and the sealed chamber 62 to about the predetermined pressures. Accordingly, should air leaks occur during operation of the apparatus 10, the air pump 116 will be activated, as necessary, to maintain the proper air pressures within the complaint support 24.

Figure 22:
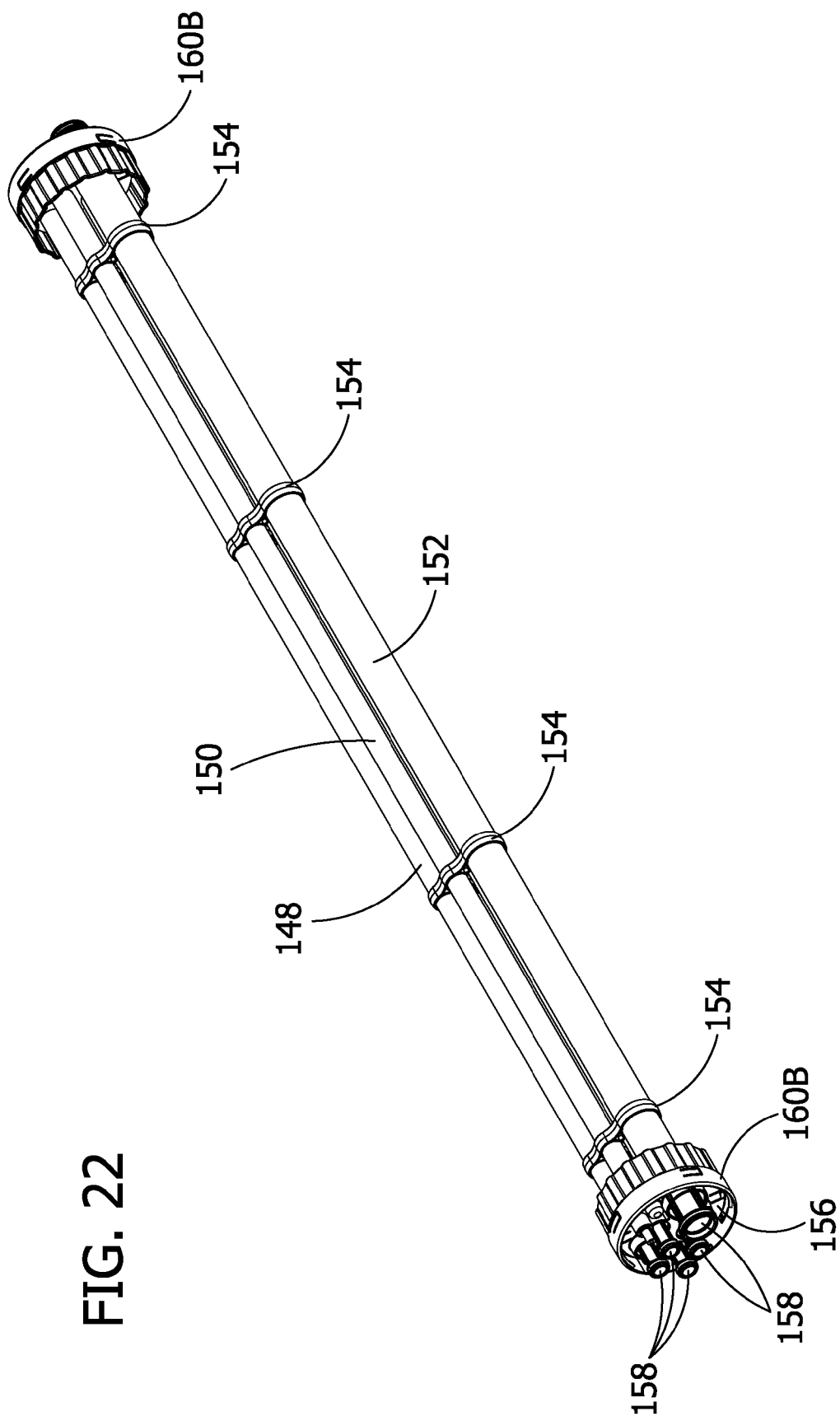
FIG. 22 is a perspective of an umbilicus for fluidly connecting the mobile cart to the cover and compliant support.
Figure 23:
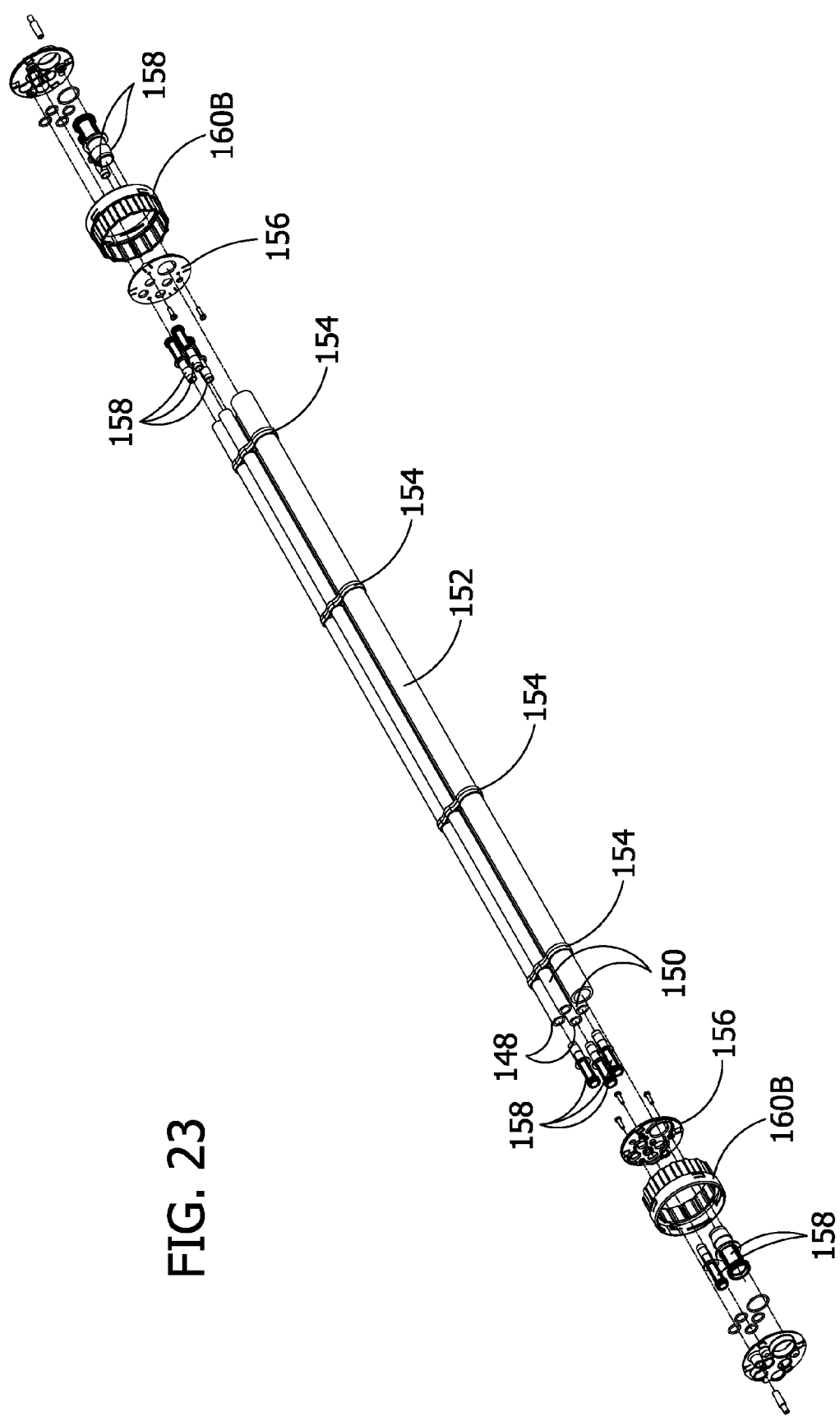
FIG. 23 is an exploded perspective of the umbilicus.

Referring to FIGS. 22 and 23, the umbilicus 120 is used to simply and easily connect the heat transfer liquid pumps 114 and the air pump 116 to the enclosure 16. The umbilicus 120 includes two flexible air supply conduits 148 for supplying air from the air pump 116 to the inflatable tubes 44A, 44B, the sealed chamber 62, and the drain tube hold-opens 84. Specifically, one of the air supply conduits 148 feeds the inflatable tubes 44A, 44B and the drain tube hold-opens 84 and the other air supply conduit feeds the sealed chamber 62. The umbilicus also includes two flexible liquid supply conduits 150 fluidly connect the heat transfer liquid pumps 114 to the enclosure 16. One of the liquid supply conduits 150 is used to feed liquid to the cover 22 and the other is used to feed liquid to the compliant support 24. The umbilicus 120 further includes a flexible liquid return conduit 152 that fluidly connects the drain tube 82 (via the weir housing 88) to the reservoir 112. The two air supply conduits 148, two liquid supply conduits 150, and liquid return conduit 152 are secured together using spaced apart retainers 154.

Each end of the umbilicus 120 comprises a quick-connect coupling 160 to attach the ends of the umbilicus and thereby the conduits 148, 150, 152 to the control system 100 and the enclosure 16 to establish a fluid connect therebetween (FIG. 2). More specifically, one end of the umbilicus 120 attaches to the weir housing 88 and the opposite end of the umbilicus attaches to the pumphead housing 140. Each of the illustrated quick-connect couplings 160 comprises a first coupling member 160A (FIGS. 13 and 18) and a second coupling member 160B (FIG. 22) selectively attachable to the first coupling member by rotating the second coupling member with respect to the first coupling member less than about 180° and more preferably less than 90°.

In the illustrated configuration, the second coupling members 160B are affixed to the ends of the umbilicus 120 (FIG. 21) and the first coupling members 160A are affixed to the weir housing 88 (FIG. 13) and the pumphead housing 140 (FIG. 18). Each of the first and second coupling members 160A, 160B comprises a manifold 156 having a connector 158 for corresponding to each of the five conduits 148, 150, 152. As a result, all five of the conduits 148, 150, 152 are connected or disconnected simultaneously by simply connecting or disconnecting the first coupling members 160A to the second coupling members 160B. It is to be understood, however, that other types of couplings including couplings besides quick-connect couplings and other types of quick-connect couplings can be used. It will also be understood that each of the conduits 148, 150, 152 can be individually connected to the control system 100 and the enclosure 14.

The apparatus 10 shown in the attached drawings is intended to be used a medical treatment facility (e.g., a hospital). The enclosure 14, for example, is sized and shaped for placement on a stretcher, such as an ambulance or emergency gurney G, to facilitate the transportation of the patient P in a conventional manner while placed in the enclosure (FIGS. 1-3). Accordingly, the enclosure 14 may have a width between about 66 centimeters (26 inches) and about 76 centimeters (30 inches) and a length between about 203 centimeters (80 inches) and about 210 centimeters (83 inches), the approximate range of dimensions for a standard ambulance or emergency gurney G. It is contemplated that the enclosure 14 may have other configurations without departing from the scope of this invention. For example, the enclosure 14 can be configured for a conventional hospital bed (not shown). It is also contemplated since many victims of cardiac arrest are initially treated by first responders (i.e., police officers, firefighters, emergency medical technicians), that the apparatus 10 can be made portable for use remote from a medical facility.

As mentioned above, the enclosure 14 is adapted to allow heat transfer liquid 18 to flow into the interior space 16 for direct contact with the patient's body to promote heat transfer between the patient P and the heat transfer liquid. To raise the temperature of a patient P, the heat transfer liquid 18 is directed into the interior space 16 of the enclosure 14 at a temperature greater than the temperature of the portion of the patient's body. For example, the heat transfer liquid 18 may have a temperature in a range of about 43° C. (109° F.) to about 47° C. (117° F.), such as about 45° C. (113° F.). One application of such a warming enclosure would be to warm a patient P suffering from unintended hypothermia.

To lower the temperature of a patient P, the heat transfer liquid 18 is directed into the interior space 16 of the enclosure 14 at a temperature lower than the temperature of the body portion of the patient received in the interior space 16 of the enclosure so that the fluid cools the body portion of the patient. For example, the heat transfer liquid 18 may have a temperature in a range of about 0° C. (32° F.) to about 5° C. (41° F.). Heat transfer liquid 18 introduced into the enclosure 14 at such a temperature has been found to cool the body at a sufficient rate to induce hypothermia while minimizing any adverse effects to the skin of the patient P. It is to be understood that temperatures other than those listed above can be used to adjust the temperature of a patient P received in the interior space 16 of the enclosure 14.

The volume of heat transfer liquid 18 necessary to effectively alter the temperature of the patient P is dependent on the size and shape of the patient. For example, a larger patient P will require more heat transfer liquid than will a smaller patient to achieve a similar rate of heat transfer. The heat transfer liquid 18 within the interior space 16 of the enclosure 14 is maintained in a relatively thin layer and near or in contact with the patient's body positioned the well 46. As a result, the amount of heat transfer liquid 18 necessary to effectively alter the temperature of the patient P can be minimized. This becomes increasingly important in remote areas where volumes of heat transfer liquid 18, which can become heavy, need to be carried by hand.

The amount of time necessary to induce hypothermia in a patient P is dependent on numerous factors including how much of the patient's body is positioned in the interior space 16 of the enclosure 14, the temperature of the heat transfer liquid 18, and the amount of time the heat transfer liquid is in contact with the patient's body. As a result, the enclosure 14 is adapted to enclose substantially the entire body of the patient's thereby providing a large portion of the patient's total surface area for heat transfer with the heat transfer liquid 18. In the illustrated configuration, the face of the patient is not enclosed.

One application of cooling would be to cool a patient P suffering from cardiac arrest. It is well recognized that organ damage can, and typically does, occur shortly after the victim has suffered cardiac arrest. As a result, it is often in the victim's best interest to quickly and effectively induce hypothermia to minimize or prevent organ damage. It is also contemplated that the apparatus 10 may be used to treat other medical conditions than those listed or have application in other medical procedures (e.g., hyperthermia, trauma, stroke, enhancements of anti-cancer therapies, surgical support, and general thermal management).

In operation, the enclosure 14 is placed in an uninflated state on a generally flat surface, such the ambulance gurney G. The compliant support 24 is fully extended to a position such that the underside of the compliant support is resting on the gurney G. If not already done, the cover 22 is removed from the compliant support 24 by disengaging the sealing portions 94, 96 to expose the center of the compliant support 24. The patient P is carefully placed on the base 42 of the compliant support 24. Using the touch screen display on the monitor 104, the user activates the controller 102. For example, as illustrated in FIG. 24, the user could press an inflate icon button 164 or a start button 166. In response, the controller 102 activates the air pump 116 to inflate the tubes 44A, 44B, the hold-open 84 for the drain tube 82, and the sealed chamber 62 to the desired pressure. As explained above, inflating the tubes 44A, 44B and the sealed chamber 62 conforms the well 46 of the complaint support 24 to the portion of the patient's body received therein.

The air pump 116 can be activated anytime during use of the apparatus 10 by pressing the inflate icon button 164 to maintain the tubes 44A, 44B, the hold-open 84 for the drain tube 82, and/or the sealed chamber 62 at the desired pressure. In one embodiment, the air pressure in the inflatable tubes 44A, 44B and the air pressure in the seal chamber 62 is monitored using pressure sensors 144 and compared to desired pressures or a range of desired pressures by the controller 102. If the pressure in the inflatable tubes 44A, 44B or sealed chamber 62 falls below a threshold pressure, the air pump 116 is automatically activated by the controller 102 to re-inflate the respective component to the desired pressure.

The cover 22 is placed on the patient P to cover the patient's body from the neck downward. The sealing portion 94 of the cover 22 and the sealing portion 96 of the compliant support 24 are engaged thereby enclosing the patient P in the interior space 16 of the enclosure 14. The temperature sensor 108 (i.e., thermometer) is connected to the patient P for measuring the core body temperature of the patient. The temperature sensor 108 is also connected to the controller 102 so that the measured body temperature of the patient P can be conveyed to the controller. As shown in FIG. 24, the patient temperature can be displayed on the monitor.

The reservoir 112 is filled with the appropriate amount of ice 122 and heat transfer liquid 18. That is, a sufficient amount of heat transfer liquid 18 is added to the reservoir 112 to reach the heat transfer fill line 128 located on the mobile cart window 126, and sufficient amount of ice 122 is added to reach the ice and heat transfer fill line 130 (see. FIG. 1). As shown in FIG. 24, the reservoir temperature can also be monitored and displayed on the monitor 104.

Using the touch screen display on the monitor 104, the delivery system 92 can be activated by pressing a run icon button 168 on the monitor. Once activated, the pumps 114 deliver heat transfer liquid 18 to the patient's body to adjust the temperature of the patient P to a selected temperature. For example, it may be desirable to quickly lower the body temperature of a patient P suffering from cardiac arrest from about 37° C. (98.6° F.) to about 33° C. (91.4° F.). As illustrated in FIG. 24, the target temperature of the patient P can be displayed on the monitor 104. Moreover, the target temperature can be adjusted upward or downward by the user using an up arrow key 172 and a down arrow key 174, respectively.

In this example, approximately 30 liters (8 gallons) of the heat transfer liquid 18 (e.g., water) and approximately 4.5 kilograms (10 pounds) of phase change material (e.g., ice) would have been added to the reservoir 112. In some instances, it may be desirable to use pre-cooled heat transfer liquid 18. The heat transfer liquid 18, which is lowered to a temperature between about 0° C. (32° F.) and about 5° C. (41° F.), is drawn from the reservoir 112 by the pumps 114 and pumped through umbilicus 120 and into the passages 32, 68 in the cover 22 and the compliant support 24 and thereby into the top and bottom of the interior space 16 of the enclosure 14.

With both pumps 114 operating, the heat transfer liquid 18 directly contacts the body of the patient P at a flow rate of about 14 liters per minute (3.7 gallons per minute). In addition to being able to pump heat transfer liquid 18 into both the top and bottom of the enclosure 14 simultaneously, the pumps 114 can be selectively operated to pump heat transfer liquid 18 only into the top of the enclosure or only into the bottom of the enclosure. In one configuration, one of the pumps 114, such as the pump supplying heat transfer liquid 18 to the passages 32 in the cover 22, can be deactivated by the user pressing a pause button 170 on the touch screen display of the monitor 104. Both pumps 114 can be deactivated by the user pushing the pause button 170 a second time. Both pumps 114 can be reactivated by the user pushing the start button 166 and/or the run icon button 168.

During operation of the pumps 114, heat transfer liquid 18 accumulates in the well 46 in the compliant support 24 such that a greater volume of heat transfer liquid accumulates in the broader region 50 of the compliant support that receives the torso than the other regions 52, 54 of the compliant support that receive the head, legs, and feet. The heat transfer liquid 18 accumulates in the interior space 16 of the enclosure 14 until it reaches a depth greater than height of the dam 87 of the weir 86, which is in fluid communication with the large diameter outlet 80. The dam 87 maintains the heat transfer liquid 18 at the target depth D of about 11 centimeters (4.5 inches), which creates a positive gauge pressure as measured at the outlet 80 of the enclosure 14 of about 1.1 kilopascals (0.16 psi). Any heat transfer liquid 18 achieving a height greater than the spillway created by the dam 87 is drained from the interior space 16 of the enclosure 14 at a flow rate equal to or greater than flow rates at which the heat transfer liquid is being driven into the interior space 16 of the enclosure 14 by the pumps 114.

The heat transfer liquid 18 is directed back into the reservoir 112 through the liquid return conduit 152 of the umbilicus 120 where it is re-cooled by the phase change material 122 before being recirculated back into the interior space 16 of the enclosure 14. Heat transfer liquid 18 is continuously recirculated through the enclosure 14 until the patient's temperature reaches or approaches the selected temperature. The patient's temperature may drop slightly after the heat transfer liquid 18 has been stopped and, as a result, it may be desirable to stop the flow of heat transfer liquid before the patient's temperature drops to the selected temperature to prevent overshoot (i.e., lowering the patient's body temperature below the selected temperature). For example, the controller 102 can be programmed to shut off the liquid delivery system when the core body temperature of the patient is within 1° C. or 2° C. of the target temperature to prevent the patient's core body temperature from falling below the target temperature. In addition, the controller 102 can be programmed to send a warning (i.e., an audio or visual alarm) to a user if the core body temperature falls below the target temperature.

Figure 16:
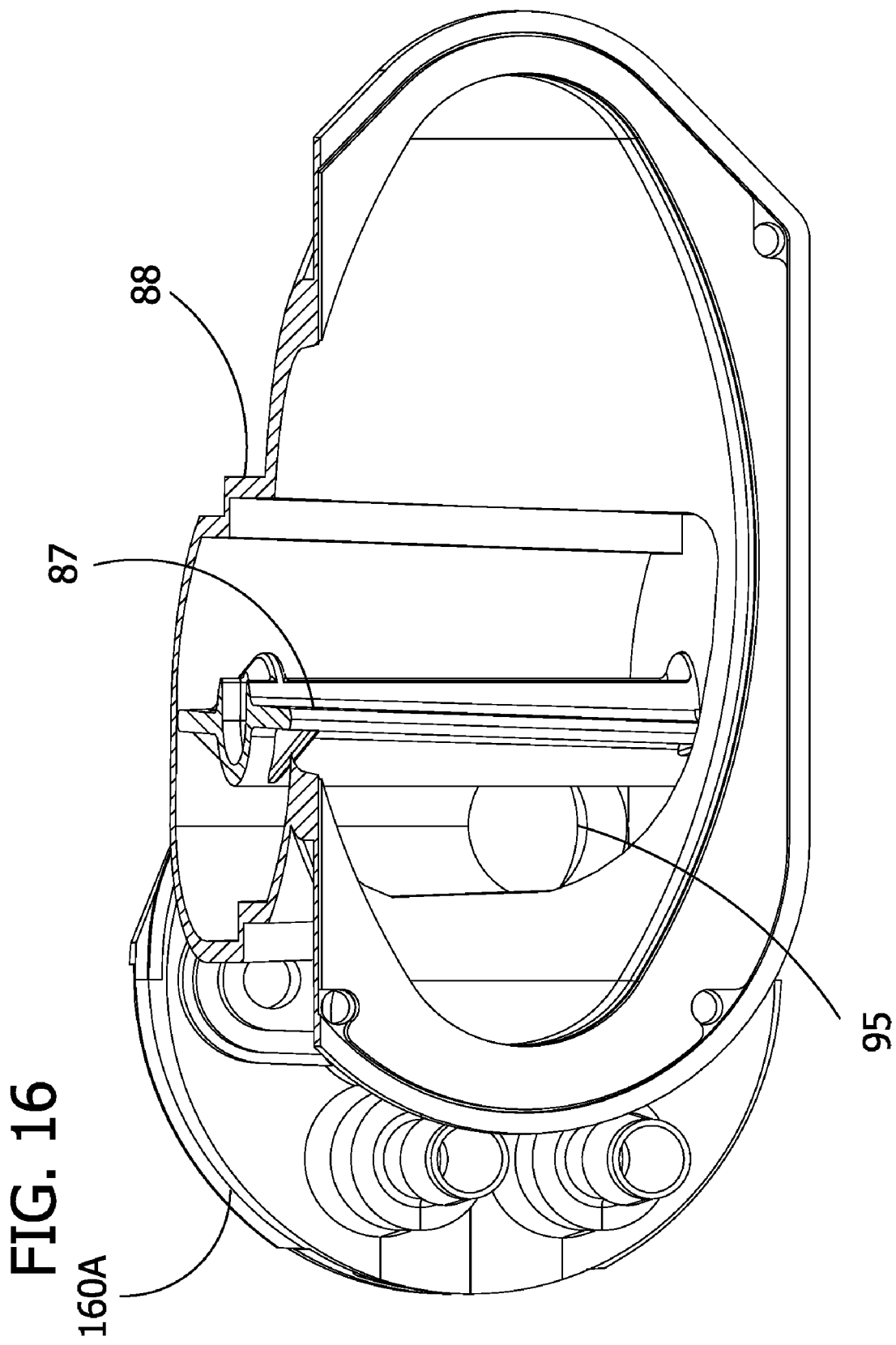
FIG. 16 is the section of FIG. 15 but showing the weir in a non-restricting position.

Once the temperature of the patient P has reached the predetermined temperature (e.g., 1° C. or 2° C. above of the target temperature), the pumps 114 are automatically shut off by the controller 102 and the heat transfer liquid 18 is purged from the enclosure 14. The interior space 16 of the enclosure 14 can also be purged by the user pressing a purge icon button 176. In yet another way, the interior space 16 of the enclosure 14 can be purged by deactivating the pumps 114 by pressing the pause button 170 twice and rotating the handle 90 on the weir 86 to move the weir from the flow restricting position (FIG. 15) to the non-restricting position (FIG. 16).

In one configuration, the interior space 16 of the enclosure 14 can be purged by allowing any heat transfer liquid 18 present in the interior space to flow via gravity through the large diameter outlet 80, through the drain tube 82 and return conduit 152, and into the reservoir 112. This is done by moving the weir dam 87 from the flow restricting position to the non-restricting position. In another configuration, the interior space 16 of the enclosure 14 can be purged by reversing the pumps 114. As a result, heat transfer liquid 18 is drawn using one of the two pumps 114 through the openings 76 in the passages 68 in the compliant support 24 and pumped back into the reservoir 112. The other pump 114 is used to draw any heat transfer liquid 18 remaining in the passages in the cover 22 back into the reservoir 112. In this configuration, the weir dam 87 can also be moved from the flow restricting position to the non-restricting position thereby allowing heat transfer liquid 18 to exit the interior space 16 of the enclosure 14 via gravity as well as via the pumps 114.

The inflatable tubes 44A, 44B, the sealed chamber 62, and the drain hold-opens 84 of the compliant support 24 can be deflated by activating the air release valves 178 (FIGS. 1 and 9). In the illustrated configuration, the air release valves 178 comprise capped plugs that can be activated by manually removing the cap from the plug housing. It is to be understood that the other types of air release valves including automated valves can be used.

If necessary, CPR can be performed on a patient P received in the interior space 16 of the enclosure 14 directly through the cover 22 while heat transfer liquid 18 is being supplied to the patient. Thus, with the cover 22 covering the patient P, oxygen can by supplied to the lungs of the patient and the chest of the patient can be compressed.

It is to be understood that during operation of the apparatus 10, the user is able to maintain visual observation of the body of the patient P through the transparent cover 22. If additional medical care is needed, the cover 22 can be partially or completely removed to expose the patient's body while the liquid delivery system remains operating. To prevent the loss of heat transfer liquid 18, the pump 114 directing heat transfer liquid to the passages 32 in the cover 22 can be shut off before the cover is pulled back. Moreover, all of the apparatus' operations can occur in the ambulance on route to the medical facility thereby not delaying any subsequent medical care.

It is to be understood that the controller 102 can be programmed so that when the user presses the start button 166 on the touch screen display of the monitor 104, the apparatus 10 automatically proceeds sequentially through the inflate, run, and purge stages of operation without further input from the user. The user, however, can interrupt operation of the apparatus 10 during any stage by pressing the pause button 170, or can completely stop the operation of the apparatus by pressing a stop button 180. The apparatus 10 can be reactivated from the paused or stopped position by the user pressing the start button 166.

The following commonly owned U.S. patents and U.S. patent applications are related to the present application and are incorporated herein by reference in their entirety: U.S. Pat. No. 6,969,399 entitled "APPARATUS FOR ALTERING THE BODY TEMPERATURE OF A PATIENT"; U.S. patent application Ser. No. 10/896,506, filed on Jul. 22, 2004 entitled "APPARATUS FOR ALTERING THE BODY TEMPERATURE OF A PATIENT"; U.S. patent application Ser. No. 10/950,152, filed on Sep. 24, 2004 entitled "APPARATUS FOR ALTERING THE BODY TEMPERATURE OF A PATIENT"; and U.S. patent application Ser. No. 10/948,918, filed on Sep. 24, 2004 entitled "APPARATUS FOR ALTERING THE BODY TEMPERATURE OF A PATIENT".

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. Apparatus for altering the body temperature of a patient, the apparatus comprising an enclosure defining an interior space for receiving at least a portion of a patient's body therein, the enclosure being constructed for transferring a heat transfer liquid into direct contact with the portion of the patient's body received in the enclosure to promote heat transfer between the patient's body and the heat transfer liquid, a drain for draining the heat transfer liquid from the interior space of the enclosure, at least a portion of the drain being disposed beneath the enclosure, and a hold-open disposed to hold the drain open to inhibit occlusion of the drain, the hold-open comprising at least one inflatable member disposed adjacent the drain to hold adjacent portions of the enclosure from occluding the drain.

2. Apparatus as set forth in claim 1 wherein the hold-open comprises two inflatable members, one of said inflatable members being located adjacent one side of the drain and the other of said inflatable members being adjacent the other side of the drain.

3. Apparatus as set forth in claim 1 wherein the enclosure is an inflatable compliant support.

4. Apparatus for adjusting the core body temperature of a patient, the apparatus comprising:
an enclosure defining an interior space for receiving at least a portion of a patient's body therein;
an inlet in the enclosure for allowing a heat transfer liquid to flow into the enclosure for direct contact with the portion of the patient's body received in the enclosure to promote heat transfer between the patient's body and the heat transfer liquid;
a liquid delivery system for directing said heat transfer liquid to flow through the inlet of the enclosure into the interior space of the enclosure; and
a control unit comprising a power source, a control system, and a user interface for powering and controlling said liquid delivery system, the control system being preprogrammed with a target temperature for the core body temperature of the patient, wherein the user interface is adapted to receive inputs from a user and comprises a button for shutting off the liquid delivery system, wherein the button has to be actuated more than once to shut off the liquid delivery system.

5. Apparatus as set forth in claim 4 wherein the control system is preprogrammed to shut off the liquid delivery system when the core body temperature of the patient reaches within 2° C. of the target temperature to prevent the patient's core body temperature from falling below the target temperature.

6. Apparatus as set forth in claim 5 wherein the control system is preprogrammed to shut off the liquid delivery system when the core body temperature reaches within 1° C. of the target temperature.

7. Apparatus as set forth in claim 4 wherein the control system is preprogrammed to send a warning to a user if the core body temperature falls below the target temperature.

8. Apparatus as set forth in claim 4 wherein the target temperature is between about 32° C. and about 34° C.

9. Apparatus as set forth in claim 4 wherein the user interface comprises an LCD touch screen.

10. Apparatus for adjusting the core body temperature of a patient, the apparatus comprising:
an enclosure defining an interior space for receiving at least a portion of a patient's body therein;
an inlet in the enclosure for allowing a heat transfer liquid to flow into the enclosure for direct contact with the portion of the patient's body received in the enclosure to promote heat transfer between the patient's body and the heat transfer liquid;
a liquid delivery system for directing said heat transfer liquid to flow through the inlet of the enclosure into the interior space of the enclosure, wherein the liquid delivery system is adapted to provide heat transfer fluid over the patient and beneath the patient; and
a control unit comprising a power source, a control system, and a user interface for powering and controlling said liquid delivery system, the control system being preprogrammed with a target temperature for the core body temperature of the patient, wherein the user interface is adapted to receive inputs from a user and comprises a button for shutting off the liquid delivery system, wherein the button has to be actuated more than once to shut off the liquid delivery system, the button being capable of stopping fluid flow completely and stopping fluid flow over the patient.

11. Apparatus for adjusting the body temperature of a patient, the apparatus comprising:
an enclosure defining an interior space for receiving at least a portion of a patient's body therein;
an inlet in the enclosure for allowing a heat transfer liquid to flow into the enclosure for direct contact with the portion of the patient's body received in the enclosure to promote heat transfer between the patient's body and the heat transfer liquid;
an outlet in the enclosure for allowing the heat transfer liquid to be exhausted from the enclosure; and
a weir in fluid communication with the outlet for maintaining the heat transfer liquid at a predetermined height in the enclosure, wherein said weir is moveable between a first position wherein the weir maintains the height of the heat transfer liquid in the enclosure at the predetermined height, and a second position wherein the weir allows the heat transfer liquid to be purged from the enclosure.

12. Apparatus as set forth in claim 11 wherein said weir is disposed in a housing.

13. Apparatus as set forth in claim 11 wherein the weir is sized to maintain the heat transfer liquid in the enclosure at a height between about 7 cm (2.8 inches) and 15 cm (6 inches).

14. Apparatus as set forth in claim 13 wherein the weir is sized to maintain the heat transfer liquid in the enclosure at a height of about 11 cm (4.5 inches).

15. Apparatus as set forth in claim 11 wherein the weir is operable to maintain a positive gauge pressure at the outlet of the enclosure at about 1.1 kilopascals (0.16 pounds per square inch).

* * * * *